(12) United States Patent
Marsden et al.

(10) Patent No.: US 6,337,074 B1
(45) Date of Patent: Jan. 8, 2002

(54) ANTI-HERPESVIRAL AGENT

(75) Inventors: Howard Sinkinson Marsden, Helensburgh; Nigel Dennis Stow, Johnstone; Gordon William McLean, Livingston, all of (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/230,405

(22) PCT Filed: Jul. 28, 1997

(86) PCT No.: PCT/GB97/02025

§ 371 Date: Jan. 25, 1999

§ 102(e) Date: Jan. 25, 1999

(87) PCT Pub. No.: WO98/04707

PCT Pub. Date: Feb. 5, 1998

(30) Foreign Application Priority Data

Jul. 26, 1996 (GB) .............................. 9615730

(51) Int. Cl.[7] ..................... A61K 39/245; A61K 39/12; A61K 38/00
(52) U.S. Cl. ............... 424/229.1; 424/231.1; 424/204.1; 435/5; 536/23.72; 530/300
(58) Field of Search ........................ 424/204.1, 229.1, 424/231.1; 435/5, 7.92, 7.94, 975; 436/548; 514/12; 530/300; 536/23.72

(56) References Cited

U.S. PATENT DOCUMENTS 5,795,778 A * 8/1998 Draper ....................... 435/326

FOREIGN PATENT DOCUMENTS

| GB | 2230011 A | 10/1990 |
|---|---|---|
| WO | 91/13175 | 5/1991 |

OTHER PUBLICATIONS

Marsden et al. 1997, Journal of Virology, vol. 71, No. 9, pp. 6390–6397, Sep. 1997.*

McLean et al., "The herpes simplex virus type 1 origin–binding protein interacts specifically with the viral UL8 protein", Journal of General Virology, vol. 75, No. 10, Oct. 1994, pp. 2699–2706.

Liptak et al., "Functional Order of Assembly of Herpes Simplex Virus DNA Replication Proteins into Prereplicative Site Structures", Journal of Virology, vol. 70, No. 3, Mar. 1996, pp. 1759–1767.

* cited by examiner

Primary Examiner—Ali R. Salimi
(74) Attorney, Agent, or Firm—Ratner & Prestia

(57) ABSTRACT

An antiviral agent capable of disrupting the association of two viral proteins required for DNA replication in herpesviruses. The agents disrupt the association of UL8 and POL in HSV-1 or the association of equivalent homologues of these proteins in other herpesviruses (for example UL 102 and UL54 in HCMV). Suitable agents are peptides which mimic the C-terminal or C-proximal portion of UL8 (or its homologues) for example the peptide IELVFTGV-LAGVWGEGGKFV. Peptidomimetic compounds of such peptides are also suitable anti-viral agents. An assay to test for agents capable of disrupting association of POL and UL8 (or homologues thereof) is also described.

3 Claims, 18 Drawing Sheets

Figure 1:
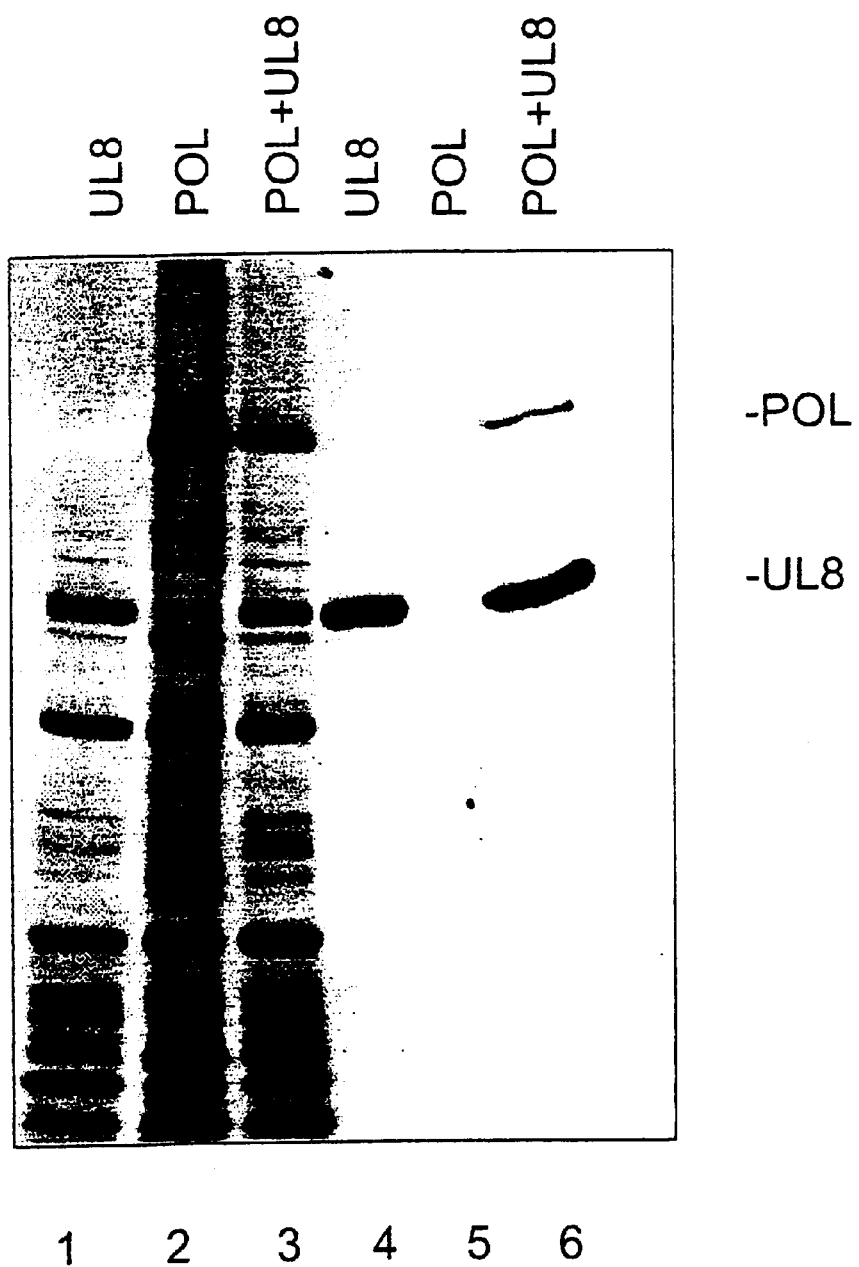

```
Peptide    7J      IVEFLKVGFGTEGGVWLVAG
                    *   *   ***    *
Peptide    7          IELVFTGVLAGVWGEGGKFV
Peptide    5             VFTGVLAGVWGEGGKFVYPFDDKMSFLFA
```

Fig. 9

SEQUENCE LISTING

<160> NUMBER OF SEQ ID NOS: 18

<210> SEQ ID NO 1
<211> LENGTH: 12
<212> TYPE: PRT
<213> ORGANISM: Artificial Sequence

```
<220> FEATURE:
<223> OTHER INFORMATION: Description of Artificial Sequence:peptide
      derived from herpes simplex virus

<400> SEQUENCE: 1

Tyr Pro Phe Asp Asp Lys Met Ser Phe Leu Phe Ala
 1               5                  10

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 2

Ala Gly Val Trp Gly Glu Gly Gly Lys Phe Val Tyr Pro Phe Asp Asp
 1               5                  10                  15

Lys Met Ser Phe Leu Phe Ala
            20

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 3

Val Leu Ala Gly Val Trp Gly Glu Gly Gly Lys Phe Val Tyr Pro Phe
 1               5                  10                  15

Asp Asp Lys Met Ser Phe Leu Phe Ala
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 4

Thr Gly Val Leu Ala Gly Val Trp Gly Glu Gly Gly Lys Phe Val Tyr
 1               5                  10                  15

Pro Phe Asp Asp Lys Met Ser Phe Leu Phe Ala
            20                  25

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 5

Val Phe Thr Gly Val Leu Ala Gly Val Trp Gly Glu Gly Gly Lys Phe
 1               5                  10                  15

Val Tyr Pro Phe Asp Asp Lys Met Ser Phe Leu Phe Ala
            20                  25
```

```
<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 6

Thr Gly Val Leu Ala Gly Val Trp Gly Glu Gly Gly Lys Phe Val
 1               5                  10                  15

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 7

Ile Glu Leu Val Phe Thr Gly Val Leu Ala Gly Val Trp Gly Glu Gly
 1               5                  10                  15

Gly Lys Phe Val
            20

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 8

Glu Ile Leu Arg Glu Ile Glu Leu Val Phe Thr Gly Val Leu Ala
 1               5                  10                  15

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 9

Ile Val Glu Phe Leu Lys Val Gly Phe Gly Thr Glu Gly Gly Val Trp
 1               5                  10                  15

Leu Val Ala Gly
            20

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 10

Val Lys Leu Trp Tyr Gln Leu Glu Lys Glu Pro Ile Val Gly Ala
 1               5                  10                  15

<210> SEQ ID NO 11
<211> LENGTH: 30
<212> TYPE: PRT
```

```
<213> ORGANISM: Artificial Sequence
<220> FEATURE:
<223> OTHER INFORMATION: Description of Artificial Sequence:peptide
      derived from herpes simplex virus

<400> SEQUENCE: 11

Asp Glu Trp Val Arg Ser Leu Ala Val Asp Ala Gln His Ala Ala Lys
 1               5                  10                  15

Arg Val Ala Ser Glu Gly Leu Arg Phe Phe Arg Leu Asn Ala
            20                  25                  30

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 12

Thr Trp Leu Glu Glu Arg Asp Glu Trp Val Arg Ser Leu Ala Val Asp
 1               5                  10                  15

Ala Gln His Ala Ala Arg Arg Val Ala Ser
            20                  25

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 13

His Leu Glu Pro Ala Phe Leu Pro Tyr Ser Val Lys Ala His Glu
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:peptide
      derived from herpes simplex virus

<400> SEQUENCE: 14

Val Leu Ser Ser Ala Leu Pro Ser Val Thr Ser Ser Ser Ser Gly
 1               5                  10                  15

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 15
attatctaga ccgctatgtt tttcaacccg                                    30

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Primer
```

```
<400> SEQUENCE: 16
tatatctaga catcatcacc gtccccagtc a                              31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 17
attaggatcc ttctgtccga ggatgaccgc t                              31

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 18
attaggatcc acgtcacacg ctaagagc                                  28
```

ANTI-HERPESVIRAL AGENT

This application is the U.S. national phase application of PCT International Application No. PCT/GB97/02025 filed Jul. 28, 1997.

The present invention relates to an anti-viral agent effective against herpesviruses and to an assay for screening for other suitable anti-viral agents.

Herpesviruses include Herpes Simplex Virus types 1 and 2 (HSV-1 and HSV-2), Human Cytomegalovirus (HCMV), Epstein-Barr Virus (EBV) and Equine herpesviruses 1 and 4 (EHV-1 and EHV-4). The term "Herpesvirus" is used herein to refer to any virus of the herpesvirus family, including viruses in the α group (e.g. HSV 1 & 2, EHV 1 & 4), the β group (e.g. HCMV) and in the γ group (e.g. EBV).

Infections due to HSV have been successfully treated for many years through use of the drug acyclovir, a nucleoside analogue. Acyclovir is relatively non-toxic to the human host since it does not adversely affect the activity of the mammalian homologue of the targeted viral protein. However, similar low toxicity regimes for treating all herpesviruses have not yet been found. Whilst HCMV is treatable via use of the drug gancyclovir (Coen, 1992) the application of this drug is limited by its toxicity, poor bioavailability and the emergence of drug-resistant variants (reviewed by Coen 1992; Haffey & Field 1995; Filley et al 1995). A low-toxicity treatment for HCMV is particularly of interest as infection by this virus can cause congenital abnormalities in the newborn exposed to the virus by maternal transmission, and is also extremely problematic to immunocompromised patients, for example patients suffering from AIDS, or those on immunosuppressive therapy for cancer or following organ transplant.

The genome of herpes simplex virus type 1 (HSV-1) encodes seven proteins essential for origin dependent viral DNA synthesis (Wu et al., 1988). The genes encoding these proteins, and their protein products, are known in the art as UL5, UL8, UL9, UL29, UL30, UL42 and UL52. (McGeoch et al., 1988). Frequently the names of the genes are italicized, eg UL5, to avoid possible ambiguities. The UL30 protein, the catalytic subunit of the heterodimeric HSV-1 DNA polymerase, is also known as POL. Homologues of all seven genes have been identified in other alphaherpesviruses and human herpesviruses 6 and 7 (HHV-6 and HHV-7). Other beta- and gammaherpesviruses encode homologues of all these proteins except UL9. For convenience the terminology of the HSV-1 proteins will be used to refer not only to that particular protein but also its equivalent in other herpesviruses. Thus, as used herein the term "UL8" refers not only to UL8 of HSV-1 itself, but also to the HCMV homolgue UL102 and to equivalent homologues in other herpesviruses. Similarly, as used herein the term "POL" (or "UL30") refers not only to POL of HSV-1 itself, but also to the HCMV homolgue UL54 and to equivalent homolgues in other herpesviruses.

The functions of these proteins and their interactions may be summarised as follows. The UL9 product is an origin-binding protein (OBP) and the UL29 product (ICP8) a single-stranded DNA binding protein. These two proteins can interact via the C-terminus of UL9 (Boehmer and Lehman, 1993; Boehmer et al., 1994). The UL30 protein (POL) and UL42 proteins comprise the catalytic and accessory components, respectively, of a dimeric DNA polymerase (reviewed by Challberg, 1991; Weller, 1991) and interact via residues at or near the C-terminus of POL (Digard & Coen, 1990; Digard et al., 1993, 1995; Marsden at al., 1994; Stow et al., 1993; Tenney et al., 1993). The UL5, UL8 and UL52 proteins form a trimeric complex that exhibits both DNA helicase and DNA primase activities (Dodson et al., 1989; Crute et al., 1989). The UL5 protein is largely responsible for DNA helicase activity (Gorbalenya et al., 1989; Zhu & Weller, 1992), and the UL52 protein contributes an essential role in DNA priming (Klinedinst & Challberg, 1994; Dracheva et al., 1995) and these two proteins can form a stable subassembly that retains both functions (Calder & Stow, 1990; Dodson & Lehman, 1991; Crute et al., 1991). The UL8 component has auxiliary effects on the DNA primase activity, stimulating primer synthesis and/or utilization on a natural-sequence single-stranded DNA template (Sherman et al., 1992; Tenney et al., 1994), and is also required for efficient nuclear entry of the trimeric complex. (Calder et al., 1992; Marsden et al., 1996). UL8 is capable of binding separately to the UL5 and UL52 proteins and can also interact specifically with UL9 (McLean et al., 1994). The latter interaction with OBP may serve to recruit the helicase-primase into an initiation complex at the viral origins.

Further evidence for the occurrence of multiple interactions between DNA replication proteins has been provided by immunofluorescence experiments. In cells infected with HSV-1 in the presence of inhibitors of viral DNA synthesis UL29 (ICP8) localises to punctate structures within the nucleus termed "pre-replicative sites" (Quinlan et al., 1984). The requirement for each of the DNA replication proteins in the formation of these sites has been studied by the use of viral mutants with defects in individual replication proteins (Liptak et al., 1996; Lukonis et al., 1996). It was observed that proteins UL5, UL8, UL9 and UL52 are all necessary for the localisation of UL29 (ICP8) into pre-replicative sites and that mutants with defects in any of the other six DNA replication genes are affected in the ability of POL to localize to these sites. Although these data suggest that the DNA polymerase holoenzyme is the last component to be recruited (Liptak et al., 1996) they do not identify the specific interactions involved in this event.

It has now been found that the protein UL8 interacts with POL. Further, it has been found that disruption of the POL/UL8 interaction is possible. Examples of molecules, monoclonal antibodies and peptides that specifically disrupt the interaction have been identified.

The present invention provides an anti-viral agent capable of combatting replication of a herpesvirus by interfering with the association of UL8 and POL (as defined above).

Both the UL8 and POL proteins of HSV-1 have been previously described in the literature (e.g. Parry et al., 1993; Gottleib et al., 1990).

Furthermore the amino acid/DNA sequences of UL8 and POL from HSV-1 are available from publically accessible Genbank and EMBL databases under Nos. P10192/M19120 and P04293/M12356 (and several other entries), respectively.

The UL8/POL association is an association between two viral proteins, that are significantly different from any protein in the mammalian host organism (for HSV-1, the host is humans). Although homologues of POL are present in mammalian cells they are considerably diverged. No cellular homologue of UL8 is known. For the virus to overcome disruption of such a viral protein: viral protein interaction a double mutation, i.e. a mutation in each of the viral proteins involved, may be required. Alternatively the range of single mutations that overcome disruption, yet allow the two proteins to interact normally may be severely restricted. The probability of such reversion occurring is thus relatively low rendering this type of interaction attractive as a potential target for therapeutic agents. Additionally, as neither UL8 nor POL have close homologues in mammalian cell metabolism, the toxicity of an agent which specifically interacts with these proteins will be low.

The anti-viral agent may be a peptide or more preferably a non-peptidal compound having peptidomimetic properties. Such a non-peptidal compound will be preferred since it will be resistant to enzymic breakdown by peptidases. Suitable anti-viral compounds may include peptides having an amino acid sequence derived from the C-terminal or C-proximal region of UL8, a functional equivalent of such a peptide, or a peptidomimetic compound therefor.

The computer program "Predict-Protein" (EMBL-Heidelberg) makes a strong prediction of the presence of an alpha-helical region near the C-terminus of HSV-1 UL8 (amino acids 709–728) with the very C-terminus (residues 729–750) predicted to be in looped or extended structures (perhaps as a "tail"). The secondary structure predictions for the C-terminal regions of the UL8 homologues of bovine herpesvirus 1 (BHV-1), human cytomegalovirus (HCMV, betaherpesvirus) and Epstein-Barr virus (EBV, gammaherpesvirus) are all similar in that an alpha-helical region of approximately 20 amino acids is strongly predicted to occur within 10–26 amino acids of the C-terminus. The most inhibitory HSV-1 peptide we have identified (peptide 7, amino acids 719–738) is derived from across the junction of the predicted alpha-helix and "tail" portions at the C-terminus of UL8 and is 20 amino acids in length. We consider it likely that the predicted conserved structures in the C-terminal regions of the other herpesvirus UL8 homologues discussed above are similarly involved in interactions with the POL homologues and peptides representing similar regions might be able to disrupt the POL/UL8 interactions in these viruses. Thus the peptide is preferably derived from the free "tail" portion and/or the α-helix portion of the C-terminus of UL8. Optionally the peptide is as small as possible, eg less than 6 amino acids, but can be eg 10,14 or more amino acids in length, particularly where the peptide is derived wholly or partially from the α-helical region of the C-terminus of UL8.

Suitable peptides are set out in Table 2. In the table of inhibitory peptides the lower the $IC_{50}$ value the greater the inhibitory activity. Peptides Nos 5 and 7 are especially effective as anti-viral agents. Peptide 7 corresponding to αα 719–738 was the most inhibitory and is preferred. Functional analogues of the peptides of Table 2 (especially Nos 5 and 7) and peptidomimetic compounds therefor are likewise suitable anti-viral agents. Peptides derived from ααs 722–738 are particularly suitable.

The anti-viral agent is preferably effective against a herpesvirus selected from HSV, HCMV, Human herpesvirus 8 (HHV8), EBV and EHV 1 & 4. HCMV is of particular interest. The antiviral agent is preferably also effective against proteins homologous to UL8 and POL (eg UL102 and UL54 respectively for HCMV). Generally the anti-viral agent will be selected to mimic at least a portion at or near the C-terminus of the UL8 homologue of the specific target virus.

In a further aspect, the present invention provides an assay to determine the ability of a test substance to interfere with the association of UL8 and POL. The assay comprises the following steps:

i) providing a first viral component;
ii) exposing said first viral component to a test substance followed by a second viral component, or exposing said first viral component to a second viral component followed by a test substance;
iii) washing to remove any second viral component and/or test substance not associated with the first viral component; and
iv) detecting the presence, and optionally determining the amount, of second viral component associated with said first viral component.

The first or second viral components may be localised on a surface, such as a blotting membrane, or an assay plate for ELISA etc. Preferably the first component is immobilised in such a manner, although the invention contemplates the possibility of the assay being carried out in solution.

The first viral component may be POL or UL8. Where the first viral component is POL, the second viral component will be UL8. Where the first viral component is UL8, the second viral component will be POL.

If the assay is to test the ability of the test substance to interfer with UL54/UL102 association, the first viral component may be UL54 or UL102. Where the first viral component is UL54, the second viral component will be UL102. Where the first viral component is UL102, the second viral component will be UL54.

Detection of the presence and/or amount of second viral component associated with the first viral component may be conducted by any convenient means. Generally detection may be via a monoclonal antibody, the presence of which is established by exposure to a second labelled monoclonal antibody in a typical ELISA-style assay. Alternatively, the second viral component may be labelled (eg radioactively) to determine its binding to the first viral component.

Suitable monoclonal antibodies (Mabs) for use in the assay of the present invention have been produced (see Examples 2 and 3) and form a further aspect of the present invention. In particular the POL-specific Mab 13185 is suitable for use in the assay of the present invention where POL of HSV-1 is the second viral component. Mabs 804 and 805 are UL8-specific Mabs and are suitable for use in the present invention where UL8 of HSV-1 is the second viral component. Hybridoma cell-lines have been deposited for Mabs 13185 and 805 at the European collection of animal cell cultures at ECACC, Porton Down, Wiltshire on Jul. 26, 1996 under Accession Nos 96072640 and 96072639 respectively.

Identification of MAb 814 as an antibody that inhibits the POL/UL8 interaction and the mapping of its epitope to between amino acids 470 and 671 suggests that the C-terminus may not be the only region of UL8 to contribute to POL binding. For the POL/UL42 interaction the C-terminus was found to contribute 75% of the binding energy (Marsden et al 1994). The relative contribution of different regions of UL8 to POL binding remains to be determined.

Figure 10:
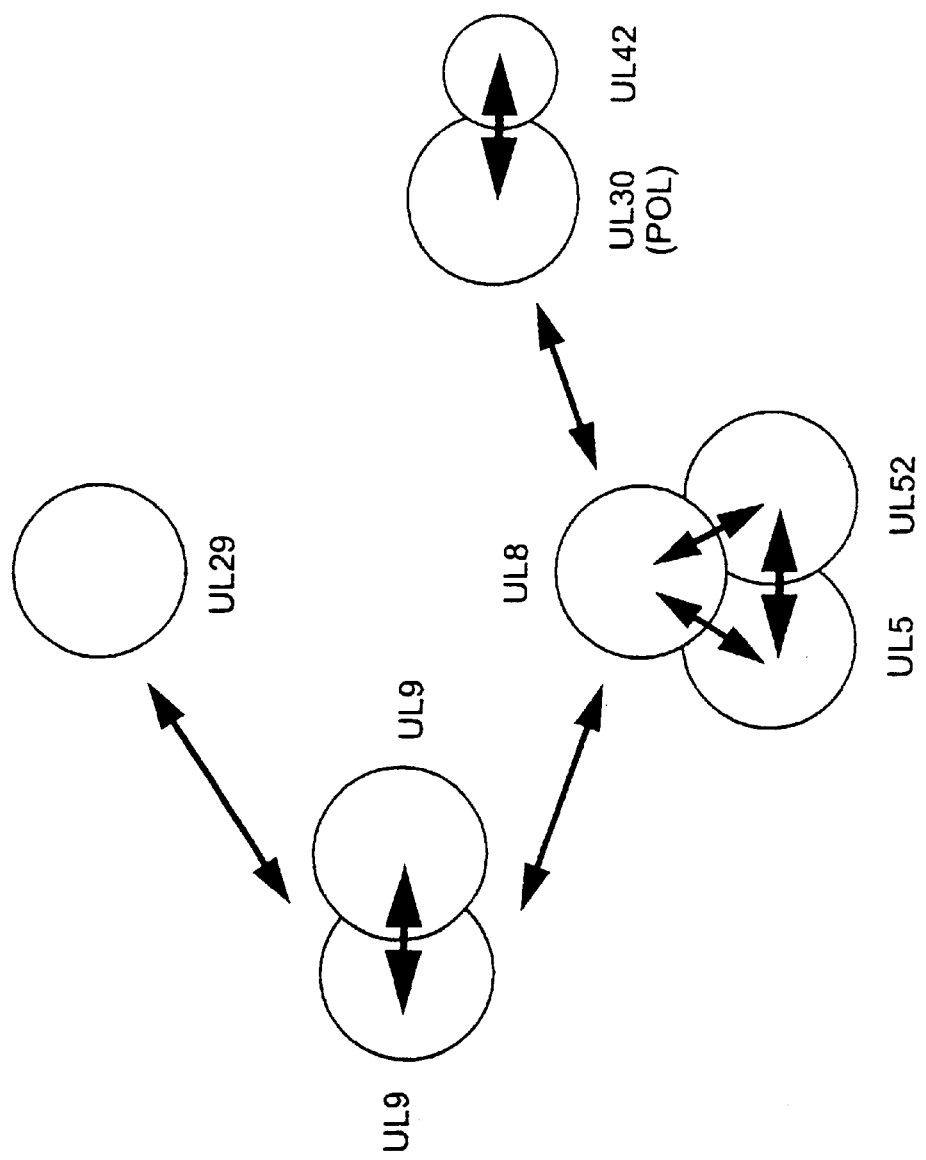

By analogy with other DNA replication systems it is considered likely that initiation of HSV-1 DNA synthesis involves the formation of an initiation complex at one or more of the replication origins. The first stage in this process would be the binding of UL9 to its recognition sequence. The interaction of UL9 with UL8 might then serve to recruit the viral helicase-primase complex (UL5, UL8 and UL52) (McLean et al., 1994). In addition, ICP8 both interacts physically with UL9 and can stimulate its helicase activity (Boehmer & Lehman, 1993; Boehmer et al., 1994). These five proteins together therefore have the potential to open up the duplex DNA in the origin region and synthesize RNA primers. The interaction between POL and UL8 which we have now identified may play an important role in bringing the viral DNA polymerase (POL/UL42 heterodimer) into the complex to initiate DNA synthesis. In addition a direct physical interaction between the polymerase and helicase-primase complexes may be important in co-ordinating the unwinding of the duplex and the synthesis of RNA primers on the lagging strand at the advancing replication fork. This model, summarized in FIG. 10, is entirely compatible with that proposed by Liptak et al. (1996) in which UL5, UL8, UL9, UL29(ICP8) and UL52 are assembled at prereplicative sites followed by recruitment of POL, which is facilitated by UL42. Our finding provides the basis for the recruitment of the POL/UL42 complex. Amongst the many questions that remain to be answered is whether the affinities of the different proteins for each other is influenced by the presence of other proteins in the complex. It is possible, for example, that binding of POL to UL8 reduces the affinity of UL8 for UL9 allowing the helicase-primase-polymerase complex to migrate away from the origin to the replication forks.

The interaction of POL with UL8 may represent a possible new target for the action of an antiviral agent. A UL8 protein lacking the C-terminal 34 amino acids is unable to support viral DNA synthesis in a transient transfection assay indicating that this region of the UL8 protein performs an essential replicative function. Although this provides evidence consistent with a key role for the UL8/POL interaction, it should be noted that we cannot exclude the possibility that this region of the protein is also necessary for some other essential function.

Our identification of peptides that block this interaction should also encourage further studies of this region and the search for more potent inhibitors. In the case of the HSV ribonucleotide reducase, following the initial discovery that peptides corresponding to the C-terminus of the small subunit inhibited enzyme activity (Cohen et al., 1986; Dutia et al., 1986), it proved possible to identify more active peptidomimetic compounds that could function intracellularly (Luizzi et al., 1994; Moss et al., 1995). The POL/UL8 interaction may be an especially attractive new target for two reasons. First, both proteins are present in infected cells in low amount in contrast to POL/UL42 and R1/R2 where one or both of the interacting proteins are abundant viral products. Second, the POL/UL8 interaction appears to be relatively weak as suggested by the observation that in contrast to POL/UL42 and R1/R2 they do not co-purify from infected cells and also by the ability of peptide 7 to block the interaction equally effectively when pre-incubation with POL was omitted. Such a weak interaction may be more readily blocked by an antiviral compound than a strong interaction.

Mabs 817, 818 and 819 all recognised peptide 5, that corresponds to residues 722 to 750 of UL8, and to a lesser extent peptide 3 (amino acids 726–750). However the Mabs do not recognise peptide 2 (amino acids 728–750) or peptide 7 (amino acids 719–738). It is therefore probable that all three MAbs recognize the same epitope located within the C-terminal 29 amino acids of UL8 and minimally involving the region spanning amino acids 727–739.

The present invention also provides a method of combatting replication of a herpesvirus, said method comprising providing an agent capable of disrupting the association UL8 and POL.

Further, the present invention provides a method of combatting an infection caused by a herpesvirus, said method comprising administering an antiviral agent as described above.

Additionally the present invention provides the use of an agent capable of interfering with association of POL/UL8 for combatting herpesvirus replication or infection.

FIGURE LEGENDS

FIG. 1. Co-precipitation of POL and UL8 protein by the UL8-specific MAb804. Lanes 1 to 3 show [$^{35}$S]-methionine-labelled extracts from Sf cells infected with AcUL8 (lane 1), AcUL30 (lane 2) or doubly with AcUL8 and AcUL30 (lane 3). The proteins precipitated from these extracts are shown in lanes 4 to 6 respectively. Proteins were separated on 8.5% SDS-polyacrylamide gels and were visualized by autoradiography. The positions of the POL and UL8 proteins are indicated.

Figure 2:
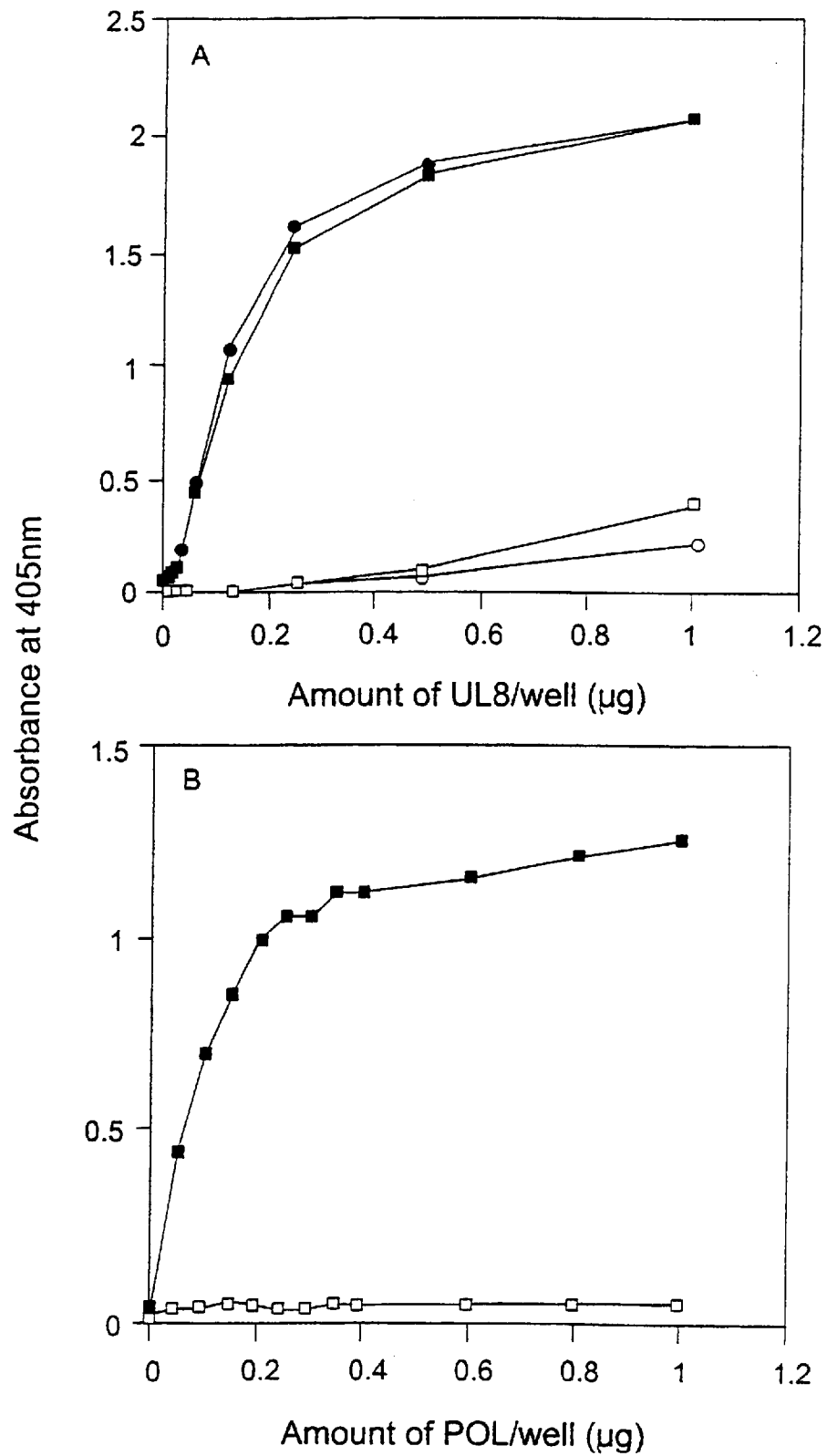

FIG. 2. POL/UL8 interaction ELISAs. Panel A. UL8 protein was added to microtiter wells pre-coated with 0.04 μg POL (●,■) or uncoated (○,□). Bound UL8 protein was detected with MAb804 (□,■) or MAb805 (○,●) which in turn were detected with an HRP-conjugated anti-mouse MAb and calorimetric substrate. Panel B. POL was added to microtiter wells pre-coated with 0.4 μg UL8 protein (■) or uncoated (□). Bound POL was detected with MAb 13185 which in turn was detected with an HRP-conjugated anti-mouse MAb and calorimetric substrate.

Figure 3:
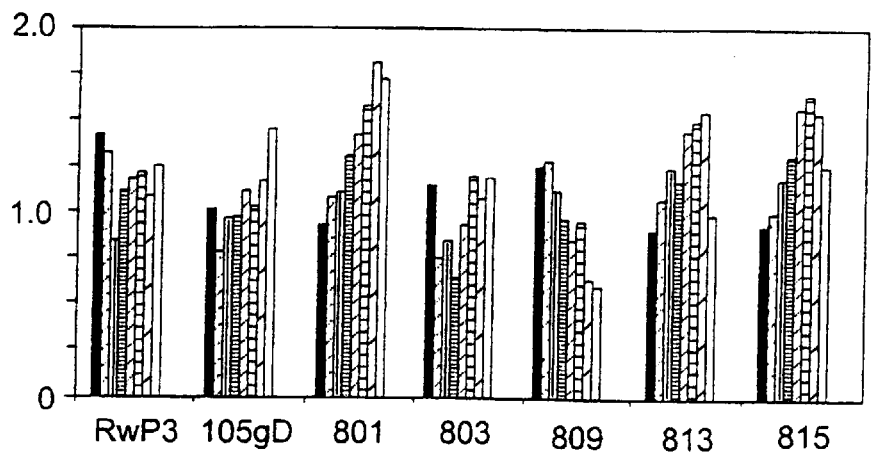
Figure 3:
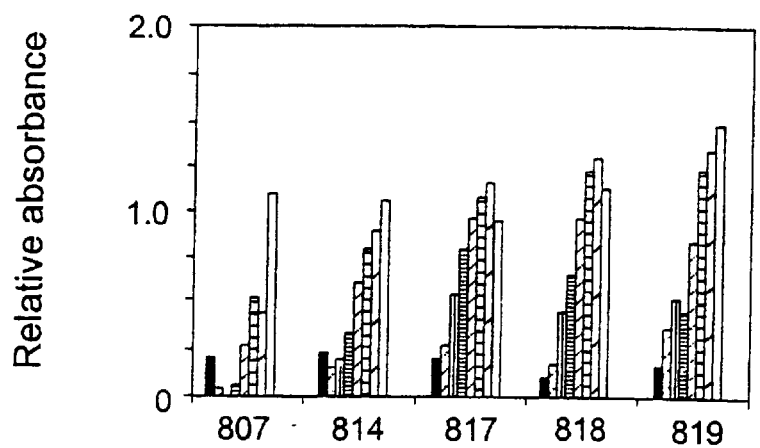
Figure 3:
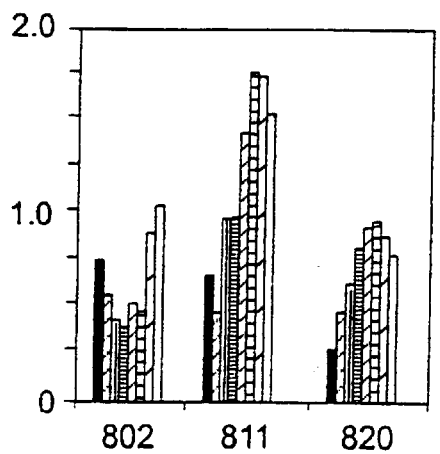

FIG. 3. Inhibition of the POL/UL8 interaction by UL8-specific MAbs. Ascitic fluid from UL8-specific MAbs and two control MAbs (RwP3 and 105gD) were serially twofold diluted and incubated for 1 h at 37° C. with 0.2 μg UL8 protein. The mixture was then added to microtiter wells coated with 0.04 μg POL. After 1 h the plates were washed and bound UL8 protein was detected with MAB 804 or MAb 805 as described. The absorbance in each well was expressed relative to that (0.945 OD units) observed in the absence of antibody. The dilutions of ascitic fluid were as follows: ■, 8-fold; ⊡, 16-fold; ⊞, 32-fold; ⊟, 64-fold; ▨, 128-fold; ⊟, 256-fold; ▨, 512-fold and □, 1024-fold. The designation of each MAb is shown below the absorbance values obtained for that MAb.

Figure 4:
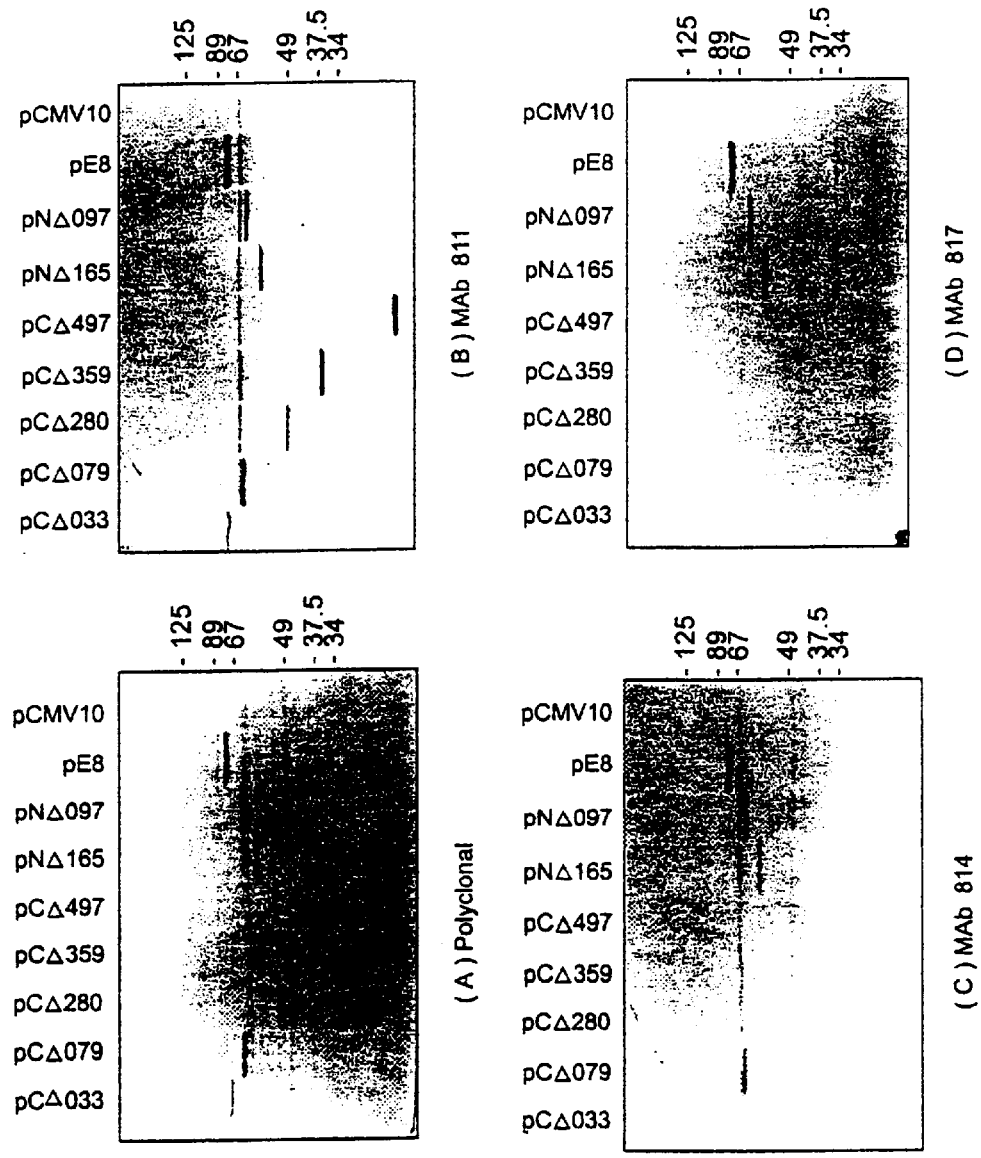

FIG. 4. Approximate mapping of the epitopes recognized by the UL8-specific MAbs. Four replicate SDS-PAGE gels were loaded with total proteins from BHK cells lipofected with the plasmids indicated. Following electrophoresis and electroblotting of the proteins onto nitrocellulose sheets the blots were incubated with 1:2000 dilutions of polyclonal anti-UL8 antiserum (a), MAb 0811 (b), MAb 0814 (c) or MAb 0817 (d). The blots were washed and incubated with 1:7500 dilutions of anti-rabbit (a) or anti-mouse (b–d) IgG alkaline phosphatase conjugated antibody and developed as described in Methods. The sizes of the prestained molecular weight markers (Sigma) are indicated.

Figure 5:
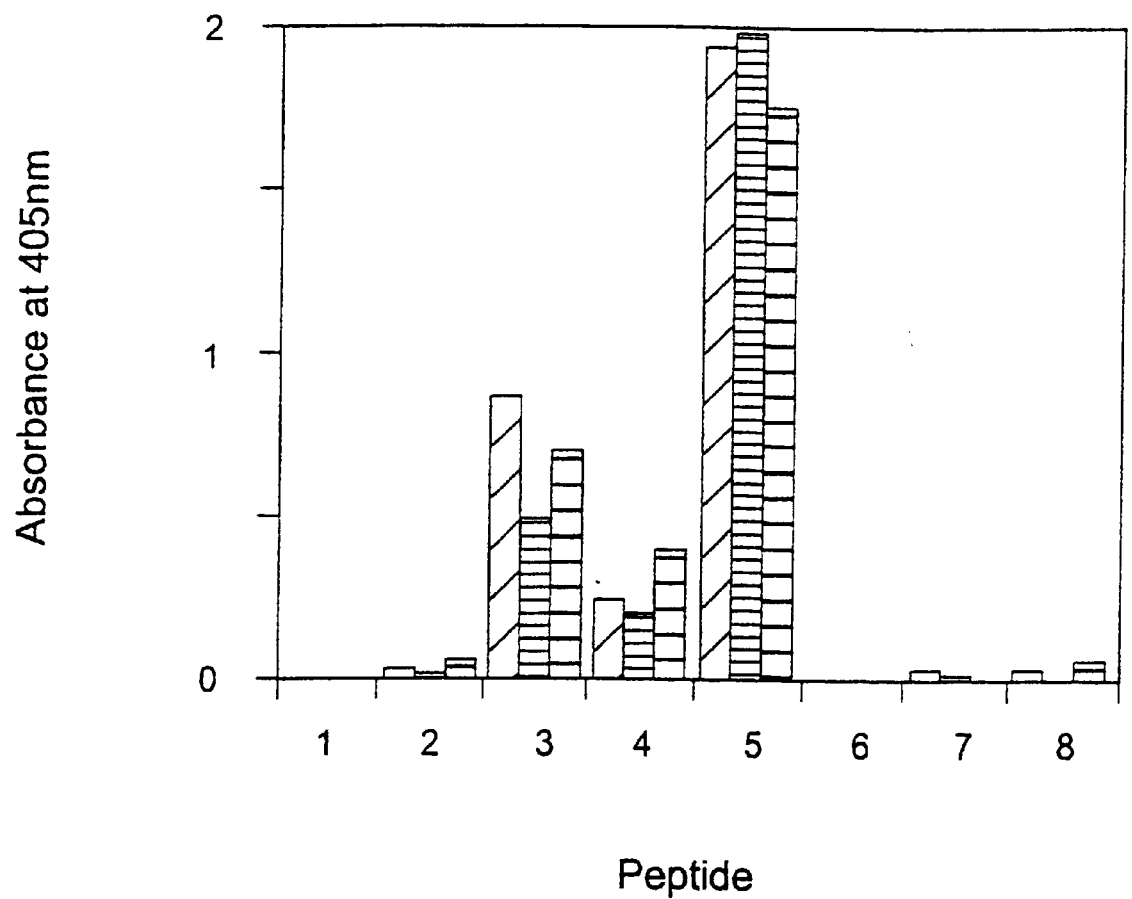

FIG. 5. Fine mapping of the epitopes recognized by MAbs 817, 818 and 819. The reactivity of the MAbs with peptides 1–8 (Table 2) was tested by ELISA. The bars show the absorbance observed with a 100-fold dilution of each MAb. The MAbs are denoted by the different cross-hatching as follows: ▨, MAb 817; ⊟, MAb 818; ⊟, MAb 819.

Figure 6:
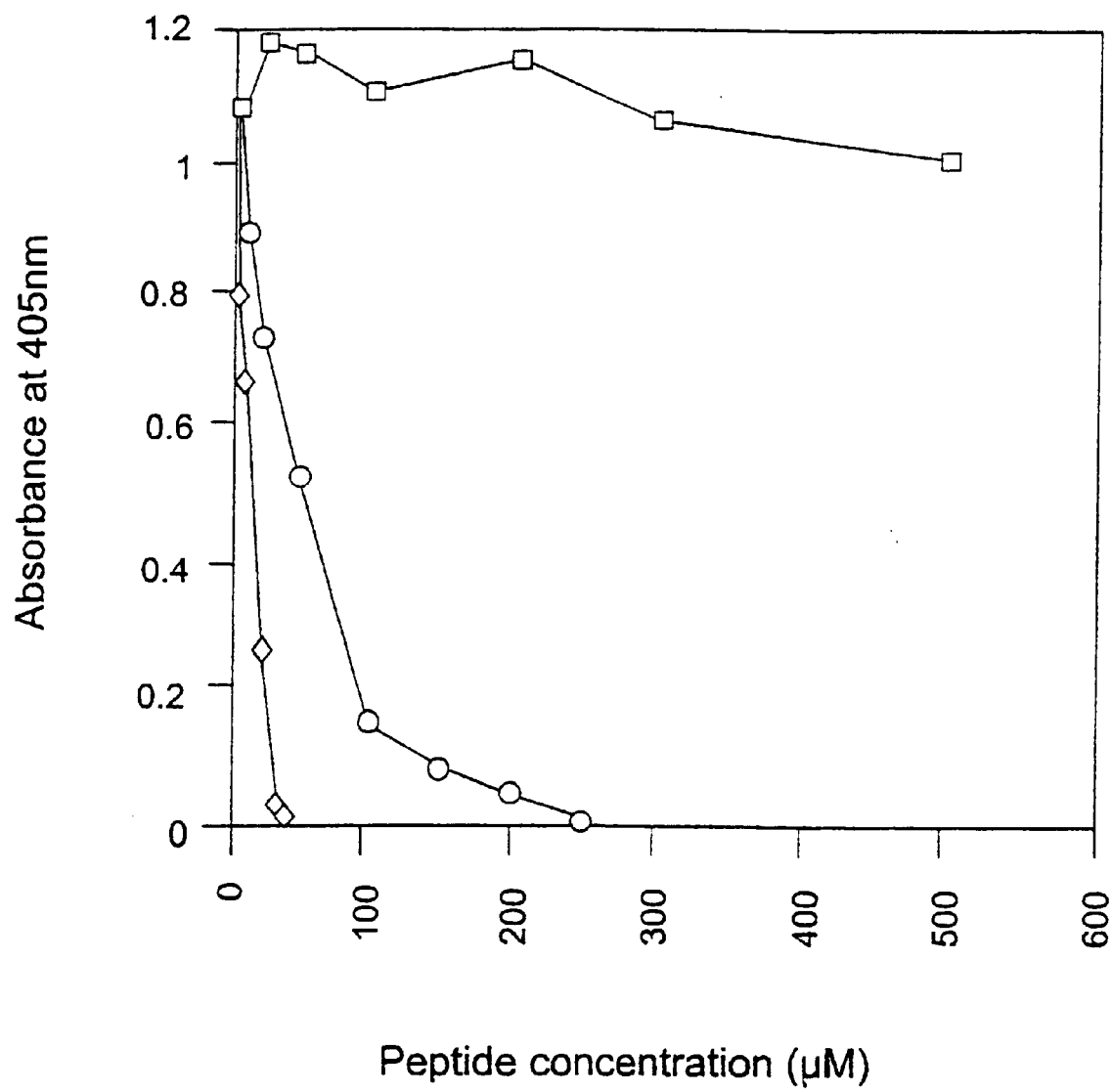

FIG. 6. Inhibition of the POL/UL8 interaction by UL8 peptides. Different concentrations of peptides 5 (○) and 7 (◇) and the control peptide RT85 (□) (Table 2) were incubated for 15 min at room temperature with 0.15 μg POL and then added to microtiter wells coated with 0.2 μg UL8 protein. After 1 h the plates were washed and bound POL was detected with MAb13185.

Figure 7:
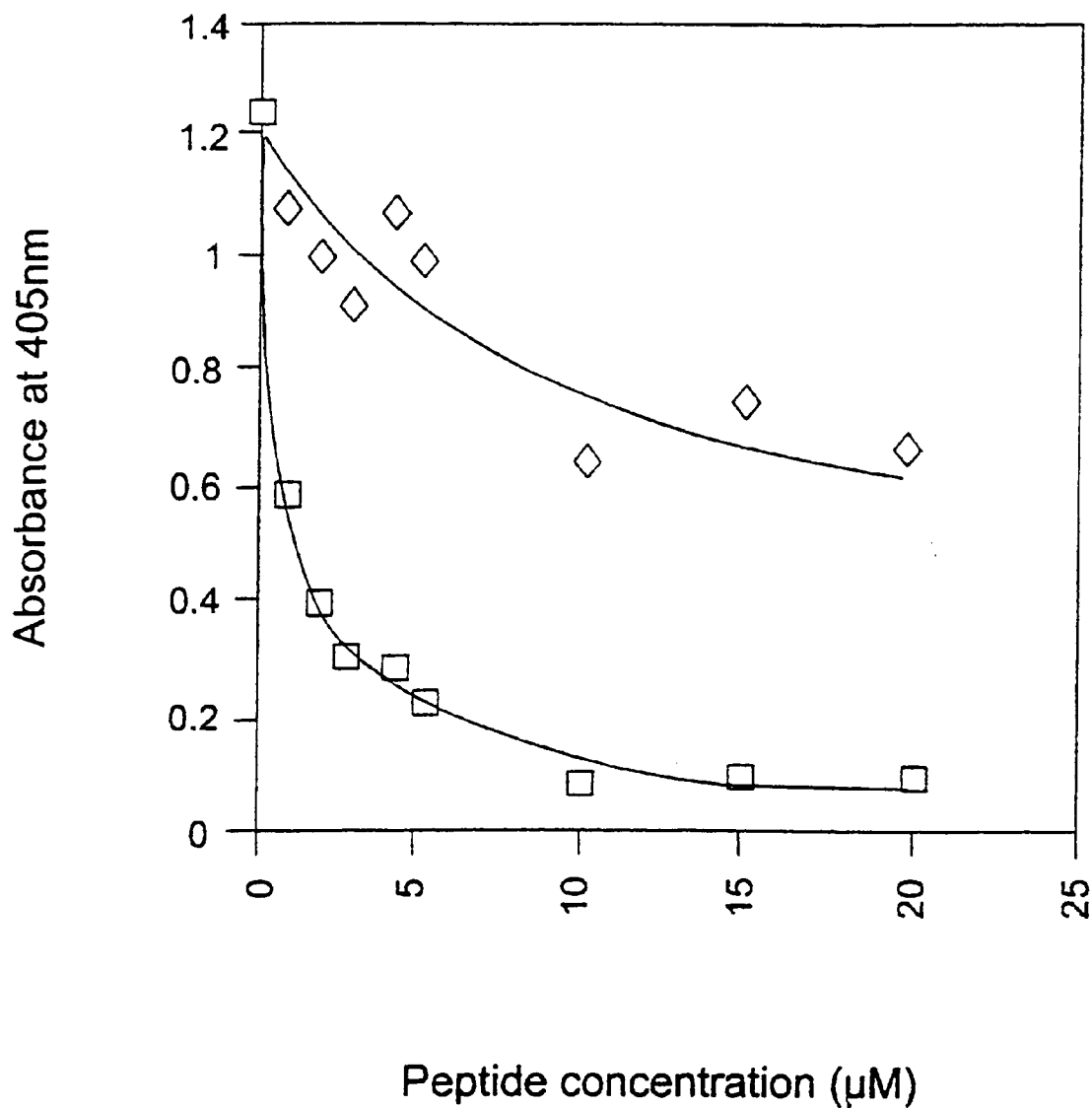

FIG. 7. The sequence of amino acids in peptide 7 is important for inhibition of the POL/UL8 interaction. Different concentrations of peptide 7 (□) and peptide 7J (◇), a jumbled version of peptide 7, (Table 2) were incubated for 15 min at room temperature with 0.15 μg POL and then added to microtiter wells coated with 0.2 μg UL8 protein. After 1 h the plates were washed and bound POL was detected with MAb13185.

Figure 8:
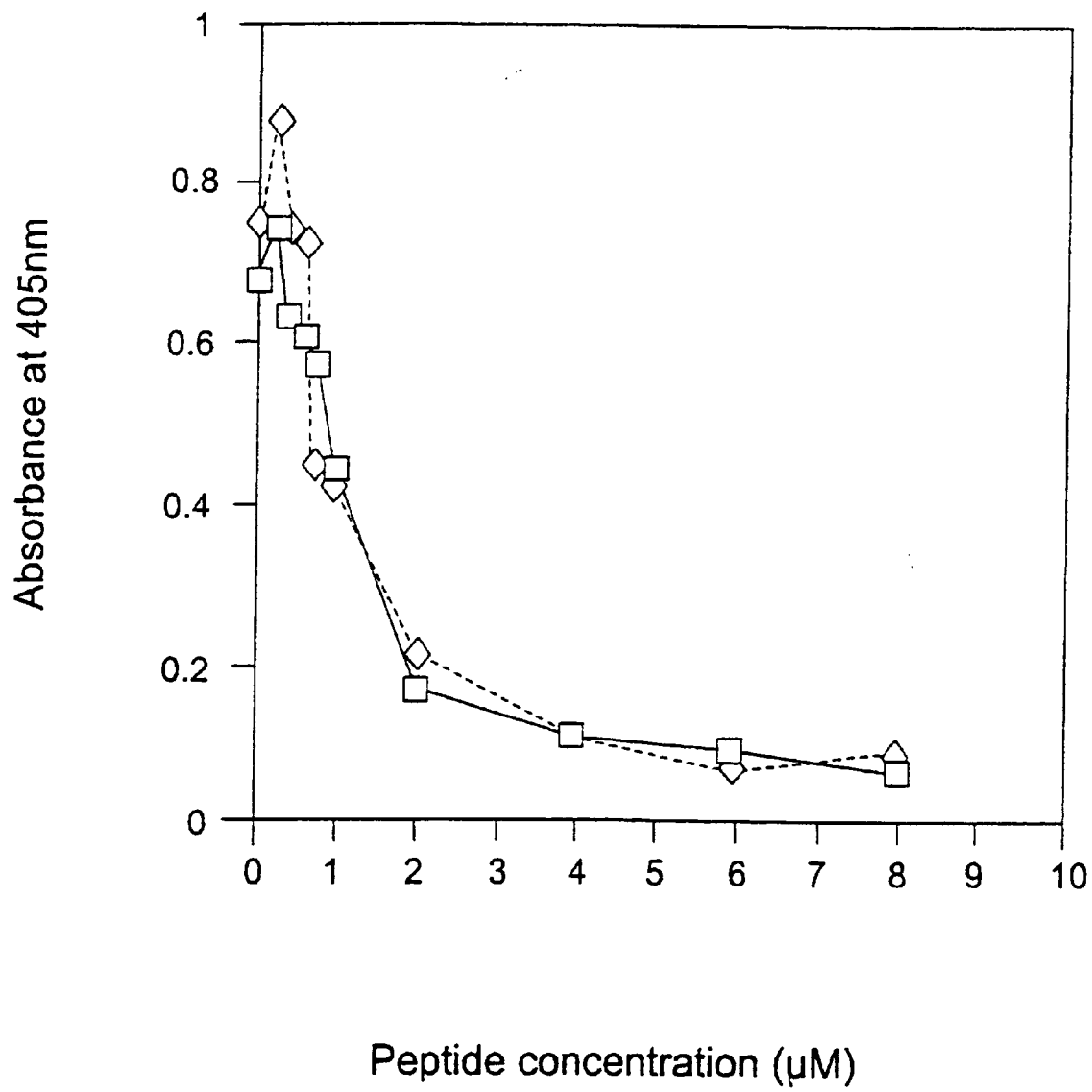

FIG. 8. Inhibition of the POL/UL8 interaction does not require prior incubation of peptide 7 with POL. Different concentrations of peptide 7 and POL (0.15 μg) were added to microtiter wells coated with 0.2 μg UL8 protein: the peptide was added either a few seconds after POL (□), or was first pre-incubated with POL for 15 min at room temperature (◇). After 1 h the plates were washed and bound POL was detected with MAb13185.

FIG. 9. Alignment of the sequences of peptides 7J, 7 and 5. The * indicates the positions at which amino acids in the three peptides are identical.

FIG. 10. Interactions between the HSV-1 DNA replication proteins. The thin, medium and thick arrows indicate relative strengths of interaction. In addition to binding to UL29 and UL8, UL9 also binds specifically to the viral replication origins. The UL9/UL29, UL9/UL8 and UL8/POL interactions are likely to be important in assembling an initiation complex at the origins following the initial binding of UL9.

Figure 11:
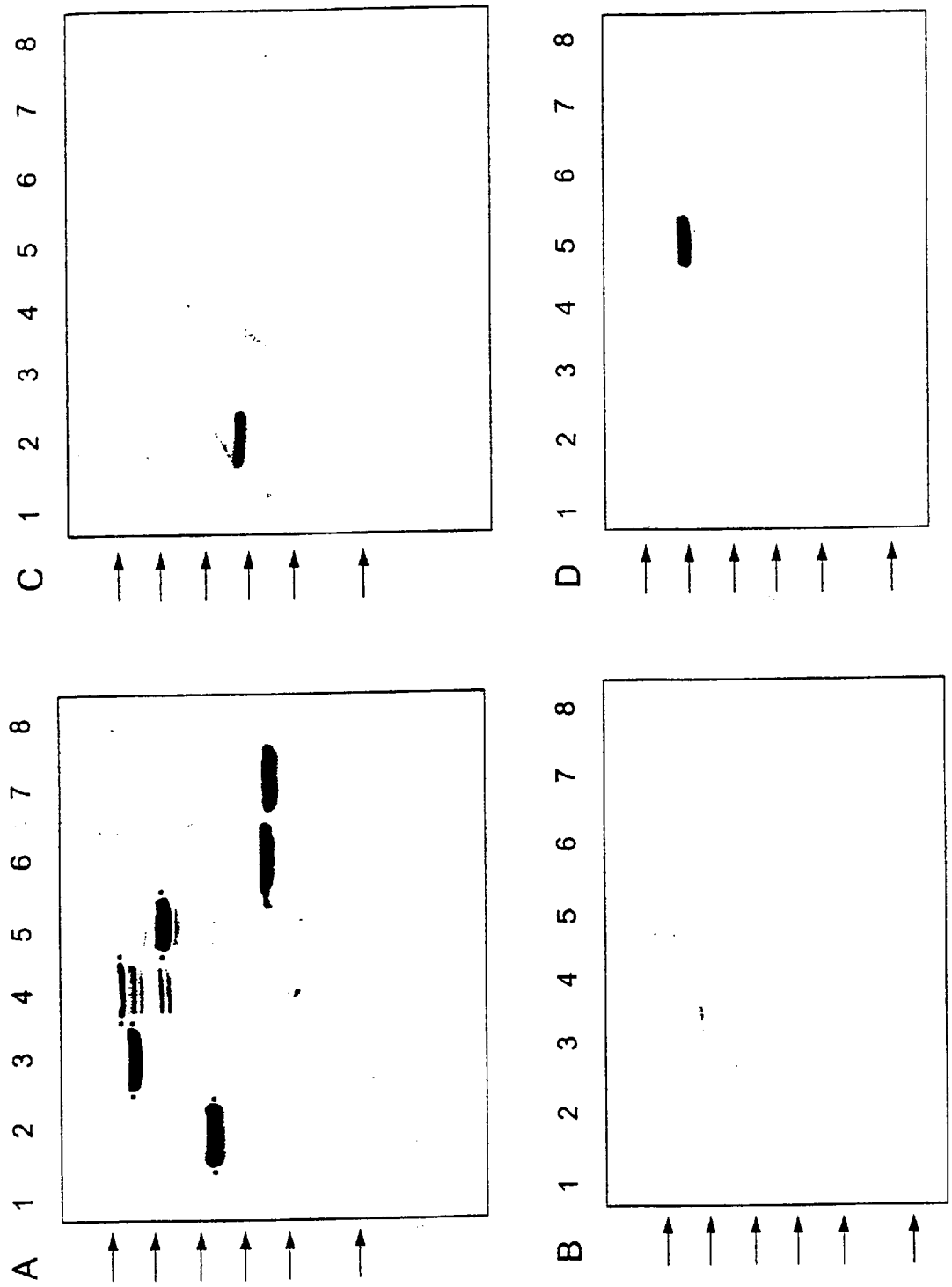

FIG. 11. Epitope mapping of POL-specific MAbs by western blotting. Extracts of *E. coli* cells expressing fragments 1–7 of gene UL30 encoding residues 1–212, 162–316, 308–658, 597–975, 875–1119, 1072–1145 and 1128–1235 respectively, were separated by SDS-PAGE (lanes 1–7). Lane 8 contains an extract from *E. coli* cells transformed with the vector pQE32 to serve as a control. Four such gels were blotted onto nitrocellulose membranes and probed with polyclonal antiserum 514 (panel A), MAb 13088 (panel B), MAb13129 (panel C) and MAb 13185 (panel D). The positions to which molecular weight markers ($M_r$s 46,000, 30,000, 21,500, 14,300, 6,500,and 3,400) migrate, are shown by arrows on the left of each panel.

Figure 12:
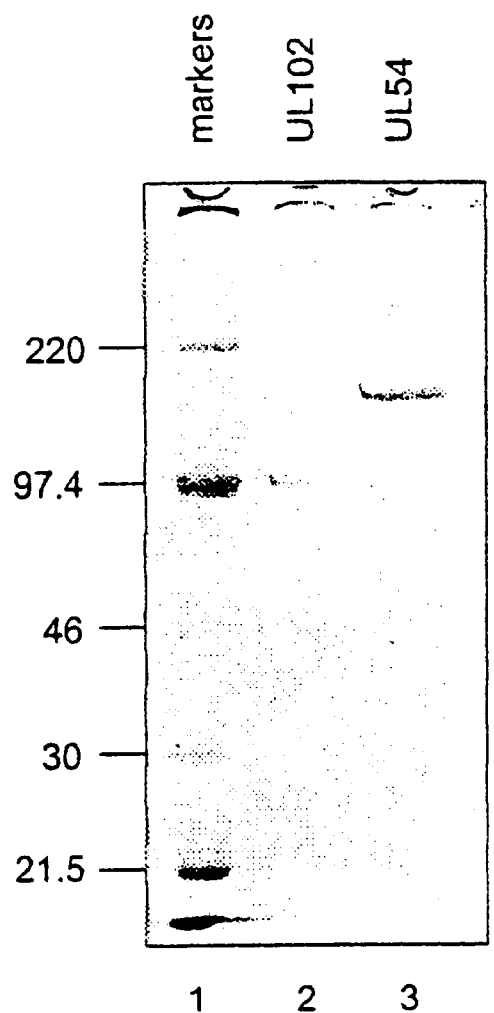

FIG. 12. Coommassie-blue stained gel of purified proteins UL102 (lane 2) and UL54 (lane 3). Proteins were separated on an SDS-10% polyacrylamide gel. The numbers to the left of the gel show the molecular weights ($\times 10^{-3}$) of the marker proteins that were electrophoresed in lane 1.

Figure 13:
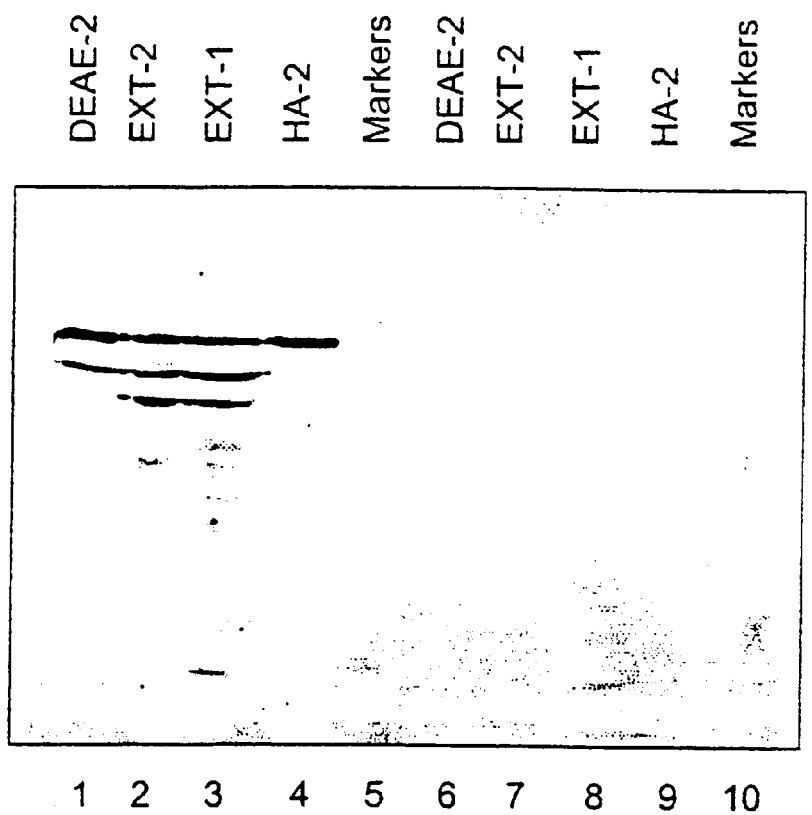

FIG. 13. Reactivity of antiserum 373, made against a peptide corresponding to amino acids 809–823 of the predicted UL102 ORF, with extracts of Sf cells infected with recombinant virus AcUL102 and proteins at different stages of purification. Proteins were separated on an SDS-10% polyacrylamide gel, transferred to a nitrocellulose membrane and reacted with antiserum 373 (lanes 1–5) or the pre-immune serum (lanes 6–10). The electrophoresed proteins were two different preparations of AcUL102-infected Sf cells (EXT-1 and EXT-2, lanes 2, 3, 7 and 8) together with peak UL102-containing fractions from the DEAE column (DEAE-2, lanes 1 and 6) and hydroxylapatite column (HA-2, lanes 4 and 9). Lanes 5 and 10 contain molecular weight markers.

Figure 14:
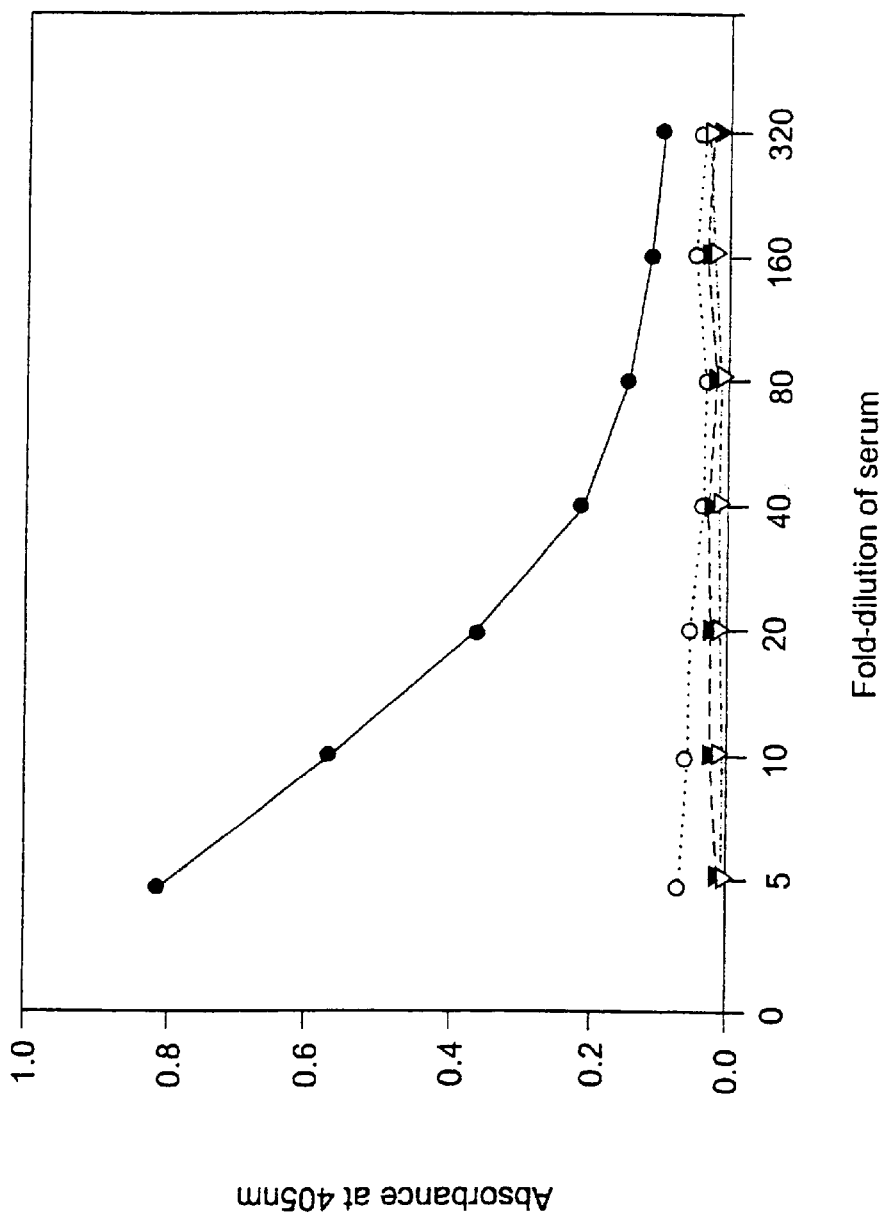

FIG. 14. Specificity of antiserum 144 for UL54. ELISA wells were coated with 0.04 mg (●,○) or 0 μg (▼,▽) of UL54 protein and reacted with antiserum 144 (●,▼) or the pre-immune serum (○,▽) as described previously (Marsden et al., 1994). The sera were initially diluted 5-fold followed by serial 2-fold dilutions. Bound antibody was detected with HRP-conjugated protein A and colorimetric substrate.

Figure 15:
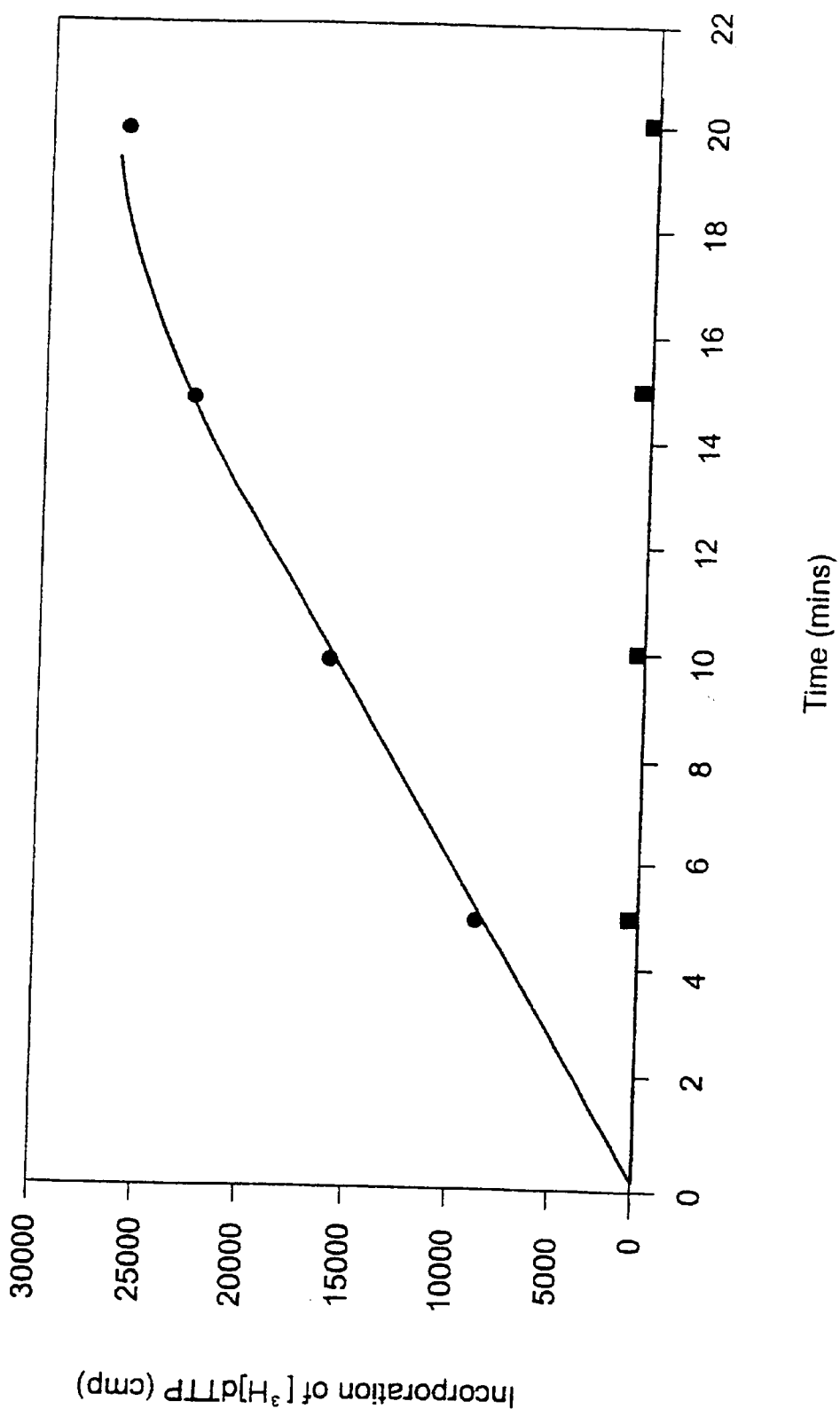

FIG. 15. DNA-dependent DNA polymerase activity of purified UL54 protein. Incorporation of [$^3$H]dTTP into an poly(dA)-oligo(dT)$_{12-18}$ template by 10 ng protein (●) or no protein (■).

Figure 16:
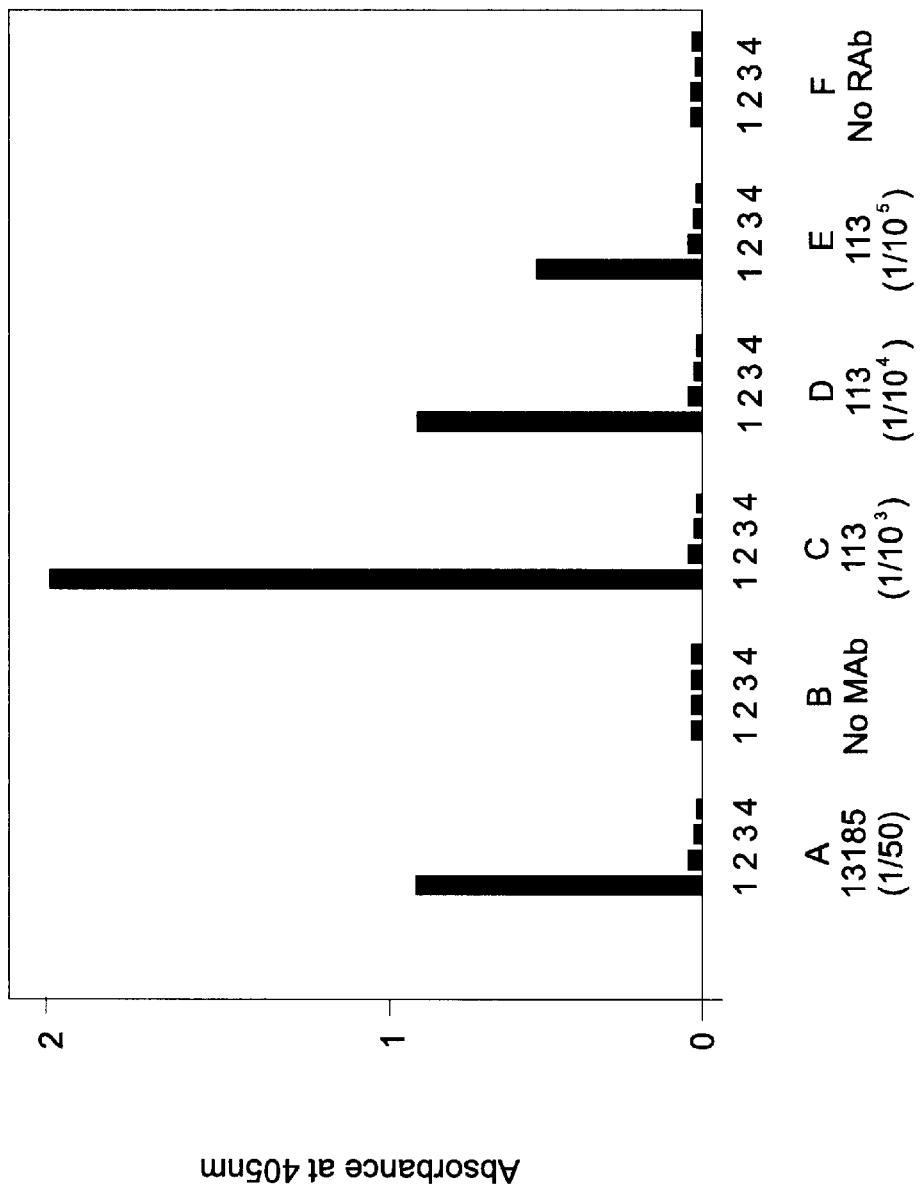

FIG. 16. The HSV-1 UL30/POL interaction can be detected by rabbit antibody 113 that was raised against the C-terminal 15 amino acids of HSV-1 UL30. The data is presented as 6 groups (A–F) each comprising 4 absorbance values (1–4). The absorbance values represent data from the interaction assay as follows: 1, both UL30 and UL8 proteins present; 2, UL8 only; 3, UL30 only; 4, both UL30 and UL8 proteins absent. The groups correspond to absorbance values produced with detecting antibodies as follows: A, MAb 13815 diluted 1/50; B, no monoclonal antibody; C–E, Rabbit antiserum 113 diluted $1/10^3$, $1/10^4$, $1/10^5$ respectively; F no rabbit antiserum. The presence of bound antibody was detected with HRP-conjugated goat anti-mouse antibody (groups A and B) or HRP-conjugated protein A (groups C–E) and calorimetric substrate.

Figure 17:
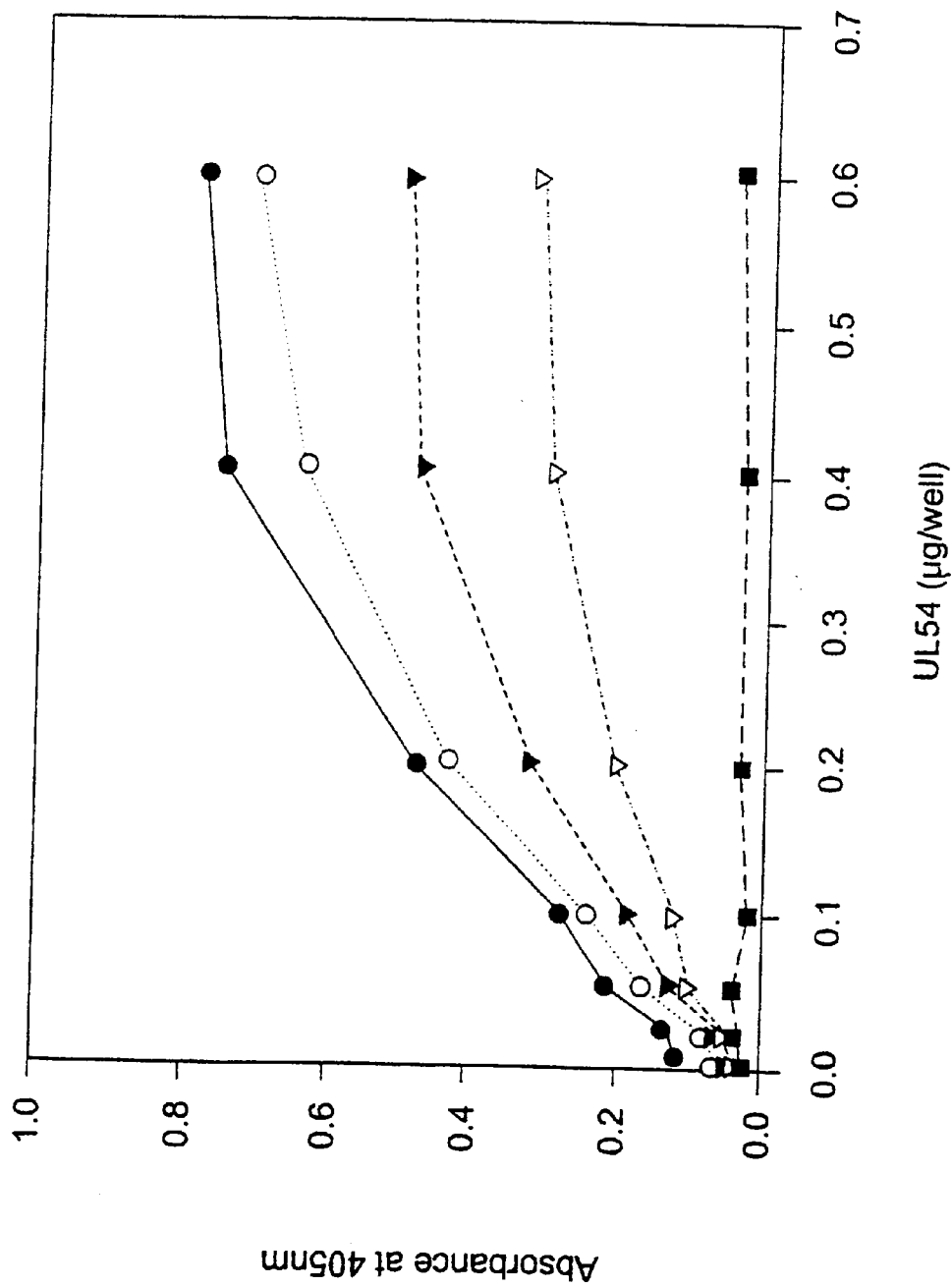

FIG. 17. UL54/UL102 interaction ELISA. UL54 protein was added to microtiter wells pre-coated with UL102 protein. The amounts of UL102 protein used to coat the wells were as follows: 0.4 μg (●), 0.2 μg (○), 0.1 μg (▼), 0.02 μg (▽), or uncoated (■). Bound UL54 was detected with rabbit antiserum 114 which in turn was detected with HRP-conjugated protein A and calorimetric substrate.

Figure 18:
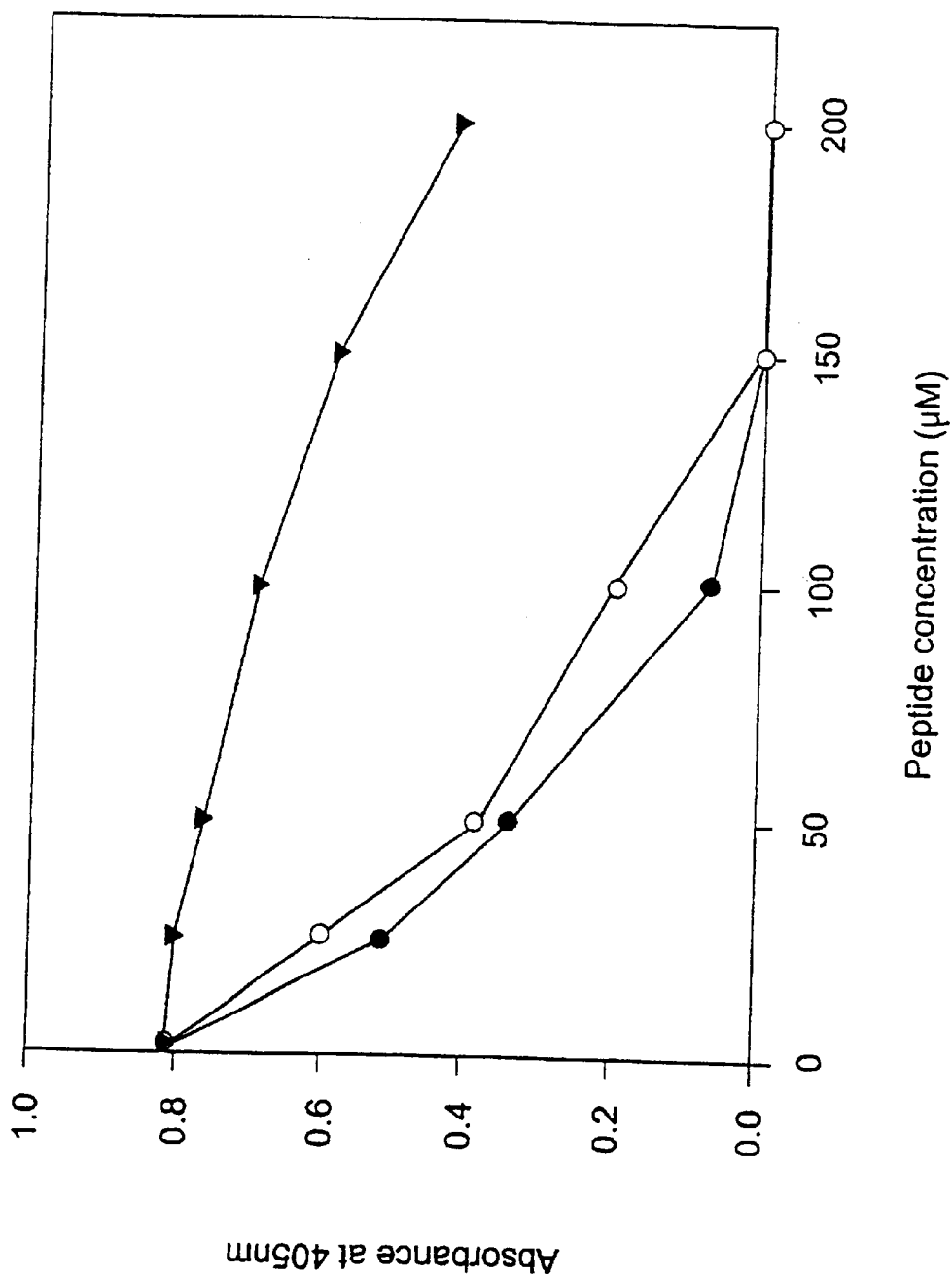

FIG. 18. Inhibition of the UL54/UL102 interaction by UL102 peptides. Different concentrations of peptides 1 (●) and 2 (○) and the control peptide RT85 (▼) (Table 4) were added with 0.4 μg UL54 to microtiter wells coated with 0.4 μg UL102 protein. After 1 h the plates were washed and bound UL54 was detected with HRP-conjugated protein A and colorimetric substrate.

| SEQUENCE LISTINGS | |
|---|---|
| SEQ ID NO 1 | Peptide 1 (Table 2) |
| SEQ ID NO 2 | Peptide 2 (Table 2) |
| SEQ ID NO 3 | Peptide 3 (Table 2) |
| SEQ ID NO 4 | Peptide 4 (Table 2) |
| SEQ ID NO 5 | Peptide 5 (Table 2) |
| SEQ ID NO 6 | Peptide 6 (Table 2) |
| SEQ ID NO 7 | Peptide 7 (Table 2) |
| SEQ ID NO 8 | Peptide 8 (Table 2) |
| SEQ ID NO 9 | Peptide 7J (Table 2) |
| SEQ ID NO 10 | Peptide RT85 (Table 2) |
| SEQ ID NO 11 | Peptide 1 (Table 4) |
| SEQ ID NO 12 | Peptide 2 (Table 4) |
| SEQ ID NO 13 | C-terminal 15 amino acids of UL54 |
| SEQ ID NO 14 | Residues 809–823 of the 873 residue UL102 |
| SEQ ID NO 15 | Primer (Example 3) |
| SEQ ID NO 16 | Primer (Example 3) |
| SEQ ID NO 17 | Primer (Example 3) |
| SEQ ID NO 18 | Primer (Example 3) |

The present invention will now be further described with reference to the following, non-limiting, examples.

EXAMPLE 1

POL/UL8 Association

Materials and Methods

Cells and recombinant baculoviruses. *Spodoptera frugiperda* (Sf) cells (strain IPLB-SF-21; Kitts et al., 1990) were maintained in TC100 medium (Life Technologies) containing 5% (v/v) fetal calf serum (FCS), penicillin (100 units/ml) and streptomycin (100 μg/ml). The *Autographa californica* nuclear polyhedrosis virus (AcNPV) recombinants AcUL30, AcUL8 (which overexpress POL and UL8 proteins respectively) have been described (Stow, 1992; 1993). Preparation and titration of virus stocks were carried out as described (Brown and Faulkner, 1977; Matsuura et al., 1987).

Antibodies. The isolation of one UL8-specific monoclonal antibody (MAb) following immunisation of mice with purified UL8 protein was described previously (McLean et al., 1994). An additional 19 MAbs were isolated from the same fusion and screened for reactivity with UL8 protein by ELISA. Ascitic fluid was prepared from cells secreting UL8-reactive antibodies. Two control MAbs were also used in these experiments: MAb RwP3 is secreted from the P3-X67-Ag8 myeloma cells (Kohler and Milstein,1975) and MAb105 gD reacts with glycoprotein D of HSV-1 (A. Cross, unpublished data). Polyclonal rabbit antiserum 094 was prepared in a Sandy Half-Lop rabbit which was immunized intramuscularly, first with approximately 25 μg purified UL8 protein (Parry et al., 1993) in Freund's complete adjuvant, followed by three boosts 10, 30 and 40 days later using the same amount of antigen but in Freund's incomplete adjuvant. The animal was sacrificed on day 50 and serum was collected.

Immunoprecipitation, immunofluorescence and Western blotting. The procedures used to prepare [$^{35}$S]-methionine labelled extracts from Sf cells infected with recombinant baculoviruses have been described in detail (McLean et al., 1994). The extracts were incubated with 1.0 μl of ascitic fluid of UL8-specific MAb804, immune complexes were captured on Protein A-Sepharose beads, proteins were separated on 8.5% SDS polyacrylamide gels and were then visualized by autoradiography as described in detail previously (McLean et al., 1994). Immunofluorescence and Western blotting were performed as described (Calder et al., 1992; McLean et al., 1994). Briefly, Sf cells infected with AcUL8 were harvested 2 days after infection, washed with PBS and solubilised with denaturing sample buffer (Laemmli, 1970), separated by 10% SDS-PAGE, and transferred to nitrocellulose membranes. The membranes were incubated with MAbs diluted from $10^2$- to $10^5$-fold, and bound antibodies were visualised using HRP coupled to anti-mouse Ig (Sigma), and chromogenic substrate 4-chloro-1-naphthol (Bio-Rad).

POL/UL8 interaction assays. ELISA assays, similar to that described for POL/UL42 (Marsden et al., 1994) were established with purified POL and UL8 proteins. POL was extracted from Sf cells infected with recombinant baculovirus AcUL30 and purified as described by Gottlieb et al. (1990) with minor modifications (Marsden et al., 1994). UL8 protein was extracted from Sf cells infected with recombinant baculovirus AcUL8 and purified as described by Parry et al., (1993) but substituting phenyl-Sepharose by hydroxylapatite chromatography (Dodson and Lehman, 1991). Both proteins were diluted in PBS to the required concentrations. For the first assay, microtiter wells were coated overnight with 0.02 μg of purified POL and blocked with 100 μl of 2% BSA in PBS for 1 h at 37° C. After blocking, the plates were washed extensively with PBS containing 0.3% Tween 20 and blotted dry. Then 50 μl of purified UL8, at the concentrations indicated in the text, were added to each well and incubated for 1 h at 37° C. Following further washes, 50 μl of UL8-specific MAb 804 or MAb 805 diluted 1:400 in PBS containing 2% FCS was reacted for 1 h at 37° C. The wells were again extensively washed and bound MAb was detected with 50 μl/well of HRP-conjugated goat anti-mouse IgG (Sigma) diluted 1:500 in PBS containing 2% FCS and chromogenic substrate ABTS. For the second assay, POL and UL8 proteins were added in the reverse order. Microtitre wells were coated overnight with 0.02 to 0.04 μg of purified UL8 protein and bound POL was detected with a POL-specific MAB 13185 (Marsden et al., 1996) diluted 1:100. Other aspects of the two assays were identical. MAbs, diluted in PBS plus 2% fetal calf serum, and peptides, diluted in 100 mM Tris-HCl (pH 8.0) plus 0.1% Tween 20, were added to the interaction assay as described in the text.

Oligopeptides. Peptides (Table 2) were synthesized by continuous flow Fmoc chemistry as previously described (Atherton and Sheppard, 1989; McLean et al., 1991). Peptides were purified by preparative reverse-phase HPLC (Owsianka et al., 1993). The Mr values of monomeric peptides were determined by matrix-assisted, laser desorption time-of-flight (MALDI-TOF) mass spectrometry and corresponded to the desired products.

Expression of fragments of UL8 and mapping UL8-specific MAbs. Plasmid pE8 contains the UL8 DNA replication gene under the control of the human cytomegalovirus major immediate early promoter in the vector pCMV10 (Stow et al., 1993) and served as parent for the construction of plasmids expressing N- and C-terminally truncated UL8 proteins, designated pNΔx and pCΔx, where x corresponds to the number of amino acids deleted (E. C. Barnard and N. D. Stow, manuscript in preparation). BHK cells (approximately 1.5×105 per 35 mm diameter petri dish) were transfected with 2 μg wild type pE8 or deletion mutant DNA using liposomes prepared as described by Rose et al. (1991). 30 h post-transfection the cells were washed with PBS and total cell proteins prepared by treating the monolayers with 150 μl denaturing sample buffer (Laemmli, 1970). Protein samples (usually 20 μl) were subjected to electrophoresis through 9% polyacrylamide gels using a Bio-Rad mini protein gel kit and electroblotted onto a nitrocellulose membrane (Towbin et al., 1979). Replicate membranes were reacted with a 1 in 2000 dilution of the MAb or with a 1 in 2000 dilution of rabbit polyclonal antiserum 094 against whole UL8 protein, and bound antibody was detected using alkaline phosphatase-conjugated anti-mouse or anti-rabbit IgG secondary antibody, as appropriate, in conjunction with the Promega Protoblot system.

Fine mapping of MAbs with peptide-based ELISA assays. Peptides were diluted in 100 mM Tris-HCl (pH 8.0) plus 0.1% Tween 20 and coated overnight onto microtiter wells at 1.0 μg/well in 50 μl. The wells were then blocked and washed as described above. MAbs were diluted 100-fold in PBS plus 2% FCS and 50 μl was added to each well and incubated for 1 h. The antibody was removed, plates were again washed and bound antibody was determined with HRP-conjugated anti-mouse IgG and colorimetric substrate as described above.

Results

Isolation and characterisation of MAbs reactive with UL8 protein. The isolation of a single MAb, (designated 0811) following immunisation of mice with purified UL8 has been described (McLean et al., 1994). From the same fusion a further 19 cell lines secreting MAbs reactive with UL8 protein were isolated. Ascitic fluid was developed for each cell line and screened for reactivity with UL8 protein in immunoprecipitation, immunofluorescence and Western blotting assays. Four of the MAbs were found to react strongly by Western blotting with protein(s) from uninfected BHK cells and were not studied further. The results obtained for the remaining 16 MAbs are summarized in Table 1.

Co-precipitation of POL with OL8. MAbs capable of immunoprecipitating UL8 protein have also been examined for their ability to co-precipitate other viral DNA replication proteins from [$^{35}$S]-methionine-labelled extracts of Sf cells mixedly infected with recombinant baculoviruses. We previously described the identification of an interaction between UL8 and UL9 using this approach (McLean et al., 1994). When extracts from Sf cells co-infected with AcUL8 and AcUL30 were reacted with MAb804, POL was found to co-precipitate with UL8 (FIG. 1, lane 6). Precipitation of POL was specific and dependent on the presence of UL8 protein since no protein of a similar size was detected in the immunoprecipitates from extracts of cells infected singly with either AcUL8 (lane 4) or AcUL30 (lane 5).

ELISAs to measure the POL/UL8 interaction. To investigate the interaction between POL and UL8 in greater detail, two separate ELISAs were developed. In one, POL was coated onto microtiter wells and binding of added UL8 was monitored with a UL8-specific MAb, while in the other assay, UL8 was coated onto microtiter wells and binding of added POL was monitored with a POL-specific MAb. The purified proteins used for the assay were essentially homogeneous as judged by SDS-PAGE analysis and coomassie blue staining: representative preparations have been shown in earlier publications (Marsden et al., 1994; Parry et al., 1993). In the first assay, binding of UL8 protein to POL-coated microtiter wells was detected with either MAb804 or MAb805 and the absorbance was dependent on the presence of the antibody (data not shown). FIG. 2A shows the characteristics of the assay and demonstrates that the amount of either MAb bound was dependent on the presence of both POL and UL8 proteins. An amount of 0.04 $\mu$g of POL was sufficient to give a good signal in this assay and was used throughout. At amounts of UL8 above 0.2 $\mu$g/well some absorbance was detected in the absence of POL. Therefore, 0.2 $\mu$g of UL8 protein per well was used in all subsequent experiments which produced an absorbance that corresponded to nearly the top of the steep initial rise.

In the second assay, the most sensitive of the POL-specific antibodies (Marsden et al., 1996) that were tested for detection of POL-binding to UL8-coated wells was MAb 13185 (FIG. 2B) and this MAb was used throughout subsequent experiments. Other POL-specific antibodies, eg. MAb 13088 and MAb 132129, gave about half the signal, while MAb 13429 and a control MAb, RwP3, gave no signal (data not shown). Again the signal was dependent on the presence of both POL and UL8 proteins (FIG. 2B) and POL-specific antibody (data not shown). Preparations of purified POL and UL8 protein were again titrated to determine the optimum amounts to be used in this assay. It was found that 0.2 to 0.4 $\mu$g/well of UL8 and 0.15 to 0.2 $\mu$g of added POL gave a good signal corresponding to nearly the top of the steep initial rise. These two ELISAs thus provide fast and convenient assays for monitoring the interaction between the two proteins.

Specific inhibition of the POL/UL8 interaction by UL8-reactive MAbs. Since it was possible that some of the MAbs reactive against UL8 might bind the molecule close to the site of interaction with POL, the UL8-specific MAbs were screened for ability to inhibit UL8 binding to POL-coated microtiter wells. Two MAbs, RwP3 and 105gD, that did not react with UL8 protein were used as controls. Doubling dilutions of each ascitic fluid were made, starting with an 8-fold dilution, and were mixed with an equal volume of UL8 protein to give a final concentration of 0.2 $\mu$g of UL8 protein per 50 $\mu$l. After incubation for 1 h at 37° C., the mixture was added to POL-coated microtiter plates and the assay was processed in the usual manner. The average absorbance in 14 wells in the absence of any MAb was 0.945 (standard deviation=0.122) and all absorbance readings were normalized to this value so that a relative absorbance of 1 corresponds to an absorbance of 0.945. The results for 13 of the UL8-specific MAbs are presented in FIG. 3 in which the relative absorbance values for each of the 8 concentrations tested for each MAb are presented as bars: the filled bar represents the 8-fold dilution and subsequent doubling dilutions are represented by progressively less densely shaded bars until the 1024-fold dilution open bar. Three patterns or reactivity were observed. The top panel contains those antibodies that did not reduce the relative absorbance below 0.50 and which were classified as non-inhibitory. The middle panel contains those antibodies that reduced the relative absorbance to less than 0.25 and were classified as inhibitory. The bottom panel contains antibodies that reduced the absorbance to between 0.25 and 0.50. This latter group of antibodies was not classified. Each antibody was tested between 2 and 4 times and the results from experiment to experiment were in good agreement. The behaviour all 16 MAbs is summarized in Table 1, which list the 5 consistently inhibitory antibodies. The epitopes recognized by those antibodies that inhibit the POL/UL8 interaction are likely to lie at or near residues on UL8 involved in its interaction with POL.

Mapping of the epitopes recognized by the UL8-specific MAbs. Seven of the 8 MAbs which detected insect cell-expressed UL8 in a Western blot were also sufficiently sensitive to allow detection of UL8 expressed in BHK cells transfected with plasmid pE8 (MAbs 809, 811, 812, 814, 817, 818 and 819). In order to determine approximate locations for the epitopes recognised, we tested their ability to detect a series of N- and C-terminally truncated UL8 molecules expressed from derivatives of pE8. Western blots, each containing an identical array of extracts from BHK cells transfected with mutated plasmids, were reacted with individual MAbs or with a polyclonal anti-UL8 antiserum (094) and representative results are shown in FIG. 4. The polyclonal serum efficiently detected each of the UL8 products (panel A). Three distinctive patterns of reactivity were observed with the MAbs indicating that the epitopes mapped to three distinct regions. MAbs 811 (B) and 812 (not shown) reacted with all the truncated proteins indicating that they recognized an epitope lying in the region of amino acids 165–253 (designated as region 1). MAbs 809 (C) and 814 (not shown) reacted with all the N-terminally truncated proteins and with products lacking up to 79 but not 280 amino acids from their C-terminus indicating the presence of an epitope between amino acids 470 and 671 (region 2). Further analysis revealed that both these MAbs were able to detect a deleted form of UL8 lacking 196 amino acids from its C-terminus thereby narrowing down the region containing the epitope(s) to amino acids 470–554 (data not shown). It is not yet known whether the MAbs recognized the same or distinct epitopes within regions 1 and 2.

MAbs 817 (D), 818 and 819 (not shown) failed to react with truncated proteins lacking 33 or more amino acids from their C-termini suggesting that they recognize one or more epitopes close to the C-terminus of UL8 (amino acids 717–750, region 3). To determine whether amino acids from this region were sufficient for recognition and to define the epitope(s) more closely series of 8 overlapping peptides that spanned and extended 3 amino acids upstream of region 3 were synthesized (Table 2) and tested for reactivity by ELISA with the MAbs. FIG. 5 shows that the three MAbs behaved identically and reacted predominantly with the C-terminal 29 amino acids of UL8 contained in peptide 5 and to a lesser extent with the slightly shorter peptides 3 and 4. Removal of 4 amino acids from the N-terminus or 12 from the C-terminus of peptide 5 reduced the signal to background levels. It is therefore probable that all three MAbs recognize the same epitope located within the C-terminal 29 amino acids of UL8 and minimally involving the region spanning amino acids 727–739.

Inhibition of the POL/UL8 interaction by UL8 peptides. The finding that all three of the MAbs (817, 818 and 819) that mapped within the C-terminal 29 amino acids of UL8 inhibited the interaction between UL8 and POL prompted us to examine the role of the C-terminal amino acids of UL8 in binding. Peptides 1–8 (Table 2) were tested for their ability to block the interaction of UL8 with POL. Peptides were dissolved in 100 mM Tris-HCl (pH 8.0) plus 0.1% Tween 20 at different concentrations and incubated with POL for 15 min to allow the peptides to bind to POL. The mixtures were then added to microtiter wells coated with UL8 and the amount of POL bound was determined after 1 h. FIG. 6 shows the results for peptides 5 and 7 and a control peptide, RT85. Peptides 5 and 7, which could not be analysed at concentrations higher than those shown because of their limited solubility, were markedly inhibitory. The control peptide was non-inhibitory, even at 500 $\mu$M. The concentration of each peptide required to reduce POL binding by 50% (the $IC_{50}$ value) was determined in at least 3, and on average 5, independent experiments. The averages of these values are listed in Table 2 together with the standard deviations for peptides 5 and 7. The different $IC_{50}$ values, ranging from 2.25 $\mu$M to non-inhibitory, suggest that the observed inhibition is peptide-specific.

To obtain additional evidence for sequence specificity of the most inhibitory peptide, an additional peptide was made that contained the same amino acids as peptide 7 but in jumbled order, and was tested for inhibition of the POL/UL8 interaction. The jumbled peptide, 7J, was made by linking residues from alternately the N- and C-termini of peptide 7. Thus, if the order of the 20 residues in peptide 7 is represented as 1, 2, 3, . . . 18, 19, 20, that in 7J was 1, 20, 2, 19, . . . 12, 10, 11. In the experiment shown in FIG. 7, the $IC_{50}$ value for peptide 7 was approximately 1 $\mu$M while peptide 7J was 20-fold less active with an the $IC_{50}$ value >20 $\mu$M.

Inhibition of the POL/UL8 interaction does not require prior incubation of peptide 7 with POL. In the previous experiment, the peptides had been pre-incubated with POL to increase the likelihood that they would inhibit its interaction with UL8 by allowing prior formation of a peptide-POL complex. We next investigated whether the preincubation step was necessary. The data presented in FIG. 8 show that the $IC_{50}$ values (approximately 1 $\mu$M) for the two curves are indistinguishable, demonstrating that inhibition does not require prior incubation with the peptide and suggesting that the POL/UL8 interaction might be a weak one.

EXAMPLE 2
Isolation and Characterization of POL-specific Monoclonal Antibodies
Materials and Methods Cells. P3-X67-Ag8 myeloma (P3) cells were grown in Dulbecco's MEM with 10% foetal calf serum, 10% horse serum, 8 mM glutamine and gentamicin. *Spodoptera frugiperda* (Sf) cells were grown at 28° C. in TC100 medium with 5% heat-inactivated foetal calf serum, antibiotics and neomycin. All reagents were supplied by Gibco/BRL and used as recommended by the suppliers except where noted.

Production and purification of proteins. POL was extracted (Gottlieb et al., 1990) from Sf cells infected with recombinant baculoviruses AcUL30 (Stow, 1992). POL protein was purified by a modification (Marsden et al., 1994) of the procedure described by Gottlieb et al. (1990).

DNA fragments encoding portions of POL were subcloned from plasmid pE30 which encodes the full length protein (Stow et al, 1993). Convenient restriction endonuclease fragments of the UL30 gene were purified and inserted in-frame into the appropriate vector from the pQE30, pQE31, pQE32 series (Qiagen). The resulting plasmids specify fusion proteins with an N-terminal extension of approximately 25 aa, including a stretch of 6 histidine residues. *E.coli* strain XL-1 blue cells (Stratagene) transformed with the following plasmids were used:—pPQ223 encoding aa 1–212 (fragment 1), pPQ101 encoding aa 162–316 (fragment 2), pPQ3 encoding aa 308–658 (fragment 3), pPQ117 encoding aa 597–975 (fragment 4), pPQ24 encoding aa 875–1119 (fragment 5), pPQ136 encoding aa 1072–1145 (fragment 6) and pPQ131 encoding aa 1128–1235 (fragment 7). XL-1 blue cells transformed with the vector pQE32 served as a control. Synthesis of the UL30 fragments was induced following treatment of *E.coli* cultures with IPTG (optimum conditions were 0.1–1.0 mM IPTG for 1–5 hours depending on the construct).

Preparation of antibodies. Donor mice for MAb production received 3 subcutaneous injections at weekly intervals, the first with complete Freund's adjuvant (CFA) and the next two with incomplete Freund's adjuvant (IFA). Three to five weeks later the mice were boosted with antigen in PBS intraperitoneally and test bled. Spleen donors received a further boost with antigen intraperitoneally four days before the fusion. Mouse spleen cells were fused to SP3 cells in the UL30 fusion using polyethylene glycol 1000. Fused cells were plated at $3 \times 10^5$ cells/well in selective medium containing HAT. Purified UL30 protein was used both for immunising donor mice and for assaying secreted antibodies by ELISA. The amount of protein for each of the 3 initial immunisations was 10 $\mu$g for POL, while for the boosts 20 $\mu$g of POL were used. ELISA assays for mouse antibodies were performed with the spent medium of growing hybridoma cells or with immunoglobulin (Ig) purified from it. Purification was achieved by precipitation of the Ig with ammonium sulphate at 50% saturation or by a more rigorous procedure whereby the medium was dilapidated with Cab-o-sil (BDH) followed by ammonium sulphate precipitation. Finally, the precipitate was dissolved in and dialysed against 20 mM Na-phosphate buffer pH7.0, and further purified using a protein G suberose column (Pharmacia): bound Ig was eluted with 0.1M glycine pH2.7, neutralised, aliquoted and stored frozen.

Polyclonal antisera 514 specific for POL was raised in rabbits by 5 intramuscular injections at fortnightly intervals, each of 5 $\mu$g of purified POL. The first immunisation was in CFA while subsequent immunisations were in IFA.

ELISA. Plates were coated at 37° C. overnight with 0.25 $\mu$g per well of purified UL30 protein: an amount chosen by initial checkerboard titrations. Tissue culture supernatants were added for 1 hour at ambient temperature. Bound antibodies were detected with horse radish peroxidase (HRP) coupled to anti-mouse Ig (Scottish Antibody Production Unit), and the chromogenic substrate ABTS (Sigma).

Western blots. Cells were solubilised with denaturing sample buffer and proteins were separated by 17.5% SDS polyacrylamide gel electrophoresis (SDS-PAGE) and transferred to nitrocellulose membranes. The membranes were incubated with purified Ig, and bound Ig was visualised using HRP coupled to anti-mouse Ig for Mabs or protein A for rabbit antibodies (both Sigma), and chromogenic substrate 4-chloro-1-naphthol (Bio-Rad). Molecular weights were estimated by comparison with standard markers (Amersham 46K–2.35K).

Immunoprecipitation. Sf cells were infected with recombinant virus AcUL30 (Stow, 1992) or parental virus AcRP23lacZ (Possie & Howard, 1987), and incubated at 28° C. overnight. Infected cells were labelled with 100 uCi/ml of [$^{35}$S] methionine (Amersham) from 24 to 31 hours post-infection (pi). They were then washed and solubilised in extraction buffer (0.5% Nonidet P40, 0.5% Na deoxycholate, 10% glycerol, 0.1M Tris HCl, pH8) for 1 hour on ice. 50$\mu$l hybridoma supernatant was incubated overnight at 4° C. with 20 $\mu$l of $^{35}$S-labelled extract and 5 $\mu$l sheep anti-mouse Ig. Complexes were precipitated with protein A Sepharose, eluted by boiling with elution buffer (2% SDS, 5% 2-mercaptoethanol, 20% glycerol, 0.125M tris HCl, pH6.8, bromphenol blue) and separated by 5–12.5% gradient SDS-PAGE.

Immunofluorescence. BHK cells grown on coverslips were infected with approximately 5 plaque forming units wt HSV-1 per cell. At 5 hour pi cells were fixed in 2% paraformaldehyde and permeabilised with 0.5% Nonidet P40. Coverslips were incubated first with the monoclonal antibody (undiluted supernatant) and then incubated with anti-mouse Ig conjugated to fluorescein isothiocyanate and examined under a Nikon microphot-SA microscope.
Results
Isolation and characterisation of POL-specific Mobs.

Fourteen hybridoma lines were developed that secreted antibodies which bound specifically to purified POL coated onto microtiter plates. These antibodies were tested for reactivity in immunoprecipitation, immunofluorescence and western blotting assays and the findings are summarised in Table 3. Eight of the 14 MAbs were positive in immunoprecipitation assays and reacted with a single major protein of the size expected for intact POL (data not shown). Of the four MAbs that were positive in immunofluorescence assays, the most strongly reactive was 13429. Eight MAbs were positive by western blotting. Three MAbs, (13185, 13429 and 13628) were reactive in all of the immunological assays.

The epitopes on POL recognised by those MAbs that reacted on western blots, were mapped using a series of seven fragments of gene UL30 that spanned the entire open reading frame. The fragments, designated 1 to 7, contained POL residues 1–212, 162–316, 308–658, 597–975, 875–1119, 1072–1145 and 1128–1235 and have expected molecular masses of 23200, 17822, 38858, 41863, 27030, 7718 and 11581 respectively. With the exception of fragment 1 with which no reactivity was observed, the POL-specific polyclonal antiserum 514 reacted with a polypeptide compatible (within the limits of SDS-PAGE) with the expected size of each of the fragments (FIG. 11) demonstrating the presence of fragments 2–7 in the extracts. The faster migrating bands reactive with antiserum 514 are probably proteolytic breakdown products of the fragments. Panels B, C and D show the specific recognition of fragments 3, 2 and 5 by MAb 13088, MAb 13129 and MAb 13185 respectively. The fragments recognised by the other western-blot reactive MAbs were determined in the same manner (data not shown) and all are listed in Table 3, together with the deduced approximate location of the epitope.

Discussion

To our knowledge, this is the first isolation and characterisation of monoclonal antibodies specific for the POL protein of HSV. Within the fourteen MAbs specific for the catalytic subunit of the DNA polymerase, eight distinct specificities can be recognised. This can be deduced from the data in Table 3, which shows that six distinct patterns of reactivities (A–F) in immunofluorescence (IF), immunoprecipitation (IP) and western blotting (WB) assays were observed. Pattern A, represented by MAbs 13185, 13429 and 13628, is formed by those MAbs that are positive in all three assays. It contains two specificities: MAbs 13185 and 13429 recognise an epitope between aa 976–1071 whereas the epitope recognised by MAb 13628 lies between aa 1120–1127. Similarly, MAb 13129, 13488 and 13528, comprising pattern B, define two epitopes.

None of the POL-specific antibodies inhibited DNA polymerase activity. The nine different epitopes recognised by the antibodies are widely spread over POL though none is located near its C-terminus. These findings are consistent with our earlier observation that the C-terminal 27 aa of POL are responsible for at least 75% of the binding energy of POL to UL42 protein. Interestingly, of the panel of 13 UL42-specific MAbs that was recently described by Scheaffer et al. (1995), all but one of the epitopes were outside the minimal active portion of the protein and none interfered with the POL/UL42 interaction.

EXAMPLE 3
Demonstration of an Interaction Between HCMV UL54 and UL102 Proteins and Inhibition of that Interaction by UL102 C-terminal and C-proximal Peptides
Methods Expression of the HCMV UL102 and UL54 gene products. Recombinant baculoviruses expressing HCMV genes UL102 and UL54 under the control of the polyhedrin promoter were generated as described below.

A 3.7 kb fragment spanning nucleotides 76904–80636 of HCMV DNA (Chee et al., 1994) and containing the HCMV UL54 ORF was amplified from a cloned copy of the HindIII F fragment of HCMV strain AD169 by PCR. The primers used were: 5'-ATTA TCTAGACCGCTATGTTTTTCAACCCG-3' and 5'-TATA TCTAGACATCATCACCGTCCCCAGTCA-3' which contained XbaI sites (underlined). The PCR-generated fragment was cleaved with XbaI and initially cloned into the XbaI site of pUC19. The XbaI fragment was then recloned into the XbaI site of the baculovirus transfer vector pAcYMX1 (Stow, 1992) downstream of the polyhedrin promoter to generate plasmid PY54. The entire XbaI fragment was sequenced to confirm the presence of the authentic UL54 gene.

A 2.7 kb fragment spanning nucleotides 146510–149208 of HCMV DNA (Chee et al., 1994) and containing the HCMV UL102 ORF was amplified from a cloned copy of the HindIII R fragment of HCMV strain AD169 by PCR. The primers used were 5'-ATTA GGATCCTTCTGTCCGAGGATGACCGCT-3' and 5'-ATTAGGATCCACGTCACACGCTAAGAGC-3' which contained BamHI sites (underlined). The PCR-generated fragment was cleaved with BamHI and cloned firstly into the pUC19 BamHI site. The UL102-containing BamHI fragment was then inserted into the BamHI site of transfer vector pAcYM1 (Matsuura et al., 1987) to generate plasmid PY102. The presence of the authentic UL102 gene was confirmed by DNA sequencing of the entire BamHI fragment.

The transfer plasmids (PY54 and PY102) were separately cotransfected with Bsu36I-cleaved DNA of the parental baculovirus AcPAK6 (Bishop, 1992) into *Spodoptera frugiperda* (Sf) cells and recombinant baculoviruses were isolated as described by Kitts et al. (1990). The presence of the desired genes was confirmed by Southern blot analysis using the amplified fragments as probes. Resulting viruses AcUL54 and AcUL102 contain the UL54 and UL102 genes, and stocks were prepared and titrated as described (Brown and Faulkner, 1977; Matsuura et al., 1987).

Purification of UL54 and UL102. Proteins UL54 and UL102 were extracted from Sf cells infected with recombinant baculoviruses AcUL54 and AcUL102 and purified as was described for the HSV-1 homologues UL30 and UL8 respectively (see POL/US interaction assays, Example 1).

Measurement of DNA polymerase activity. Activity was measured by incorporation of [$^3$H]dTTP into a poly(dA)-oligo(dT)$_{12-18}$ template using a concentration of 50 mM KCl, previously found to be optimal for the HCMV enzyme (Ertl et al., 1991). The reaction mixture (final vol. 100 µl)

contained 75 mM Tris HCl pH 8.0, 1.67 mM 2-mercaptoethanol, 6.5 mM $MgCl_2$, 1 μg poly (dA)-oligo (dT), 50 mM KCl, 40 μg BSA and 10 ng UL54 protein (HCMV DNA polymerase). Reactants were mixed on ice and the reaction was initiated by addition of 1.7 μM $^3$H-dTTP (specific activity 3.75 Ci/mmol) and transfer to 37° C. Samples of 10 μl were taken 5, 10, 15 and 20 minutes later, and spotted onto Whatman DE81 ion exchange discs which had been soaked in 0.1M EDTA and air dried. The discs were given three 10 minute washes with 5% $Na_2HPO_4$, two 5 minute washes with water and two 30 second washes with methylated spirits. They were air dried and counted in a scintillation counter with 5 ml of Ecoscint A (National Diagnostics, Kimberley Research).

Oligopeptides. Peptides were synthesized by continuous flow Fmoc chemistry as previously described (Atherton and Sheppard, 1989; McLean et al., 1991). The peptides listed in Table 4 were purified by preparative reverse-phase HPLC. The relative molecular masses of the purified peptides was determined by matrix-assisted, laser desorption time-of-flight mass spectrometry and corresponded to the desired products.

Antibodies. The hybridoma cell line that secretes monoclonal antibody (MAb) 13815 has been deposited with the European Collection of Cell Cultures (reference number 96072640). Antiserum 113, specific for HSV-1 UL30 (POL), was raised against a peptide corresponding to the C-terminal 15 amino acids of the protein and has been described previously (Marsden et al., 1994). Antiserum 144, specific for HCMV UL54 protein, was raised in rabbits-against peptide HLEPAFLPYSVKAHE that corresponds to the C-terminal 15 amino acids (residues 1226–1240) of UL54. Antiserum 373, specific for HCMV UL102 protein, was raised in rabbits against peptide VLSSALPSVTSSSSG that corresponds to residues 809–823 of the 873 residue UL102. The peptides were made as multiply antigenic peptides (Tam, 1988) of general structure (peptide sequence)$_4$K$_3$A as such peptides have been shown to generate sera with higher anti-protein titers (McLean et al., 1991).

UL54/UL102 interaction assays. ELISA assays, similar to those described for HSV-1 POL/UL8 (see Example 1 above) were established with purified HCMV UL54 and UL102 proteins. Both proteins were diluted in PBS to the required concentrations. For the assay, microtiter wells were coated overnight with purified UL102, at the concentrations indicated in the text, and blocked with 100 μl of 2% BSA in PBS for 1 h at 37° C. After blocking, the plates were washed extensively with PBS containing 0.3% Tween 20 and blotted dry. Then 50 μl of purified UL54, at the concentrations indicated in the text, were added to each well and incubated for 1 h at 37° C. Following further washes, 50 μl of UL54-specific antiserum, diluted in PBS containing 2% FCS was reacted for 1 h at 37° C. The wells were again extensively washed and bound antibody was detected with 50 μl/well of HRP-conjugated protein A (Sigma) diluted 1:500 in PBS containing 2% FCS. After further washes, chromogenic substrate ABTS was added. Peptides, diluted in 100 mM Tris-HCl (pH 8.0) plus 0.1% Tween 20, were added to the interaction assay as described in the text.

Results

Nucleotide sequence of HCMV gene UL102. Our independently determined sequence of the entire cloned fragment that spanned nucleotides 146510–149208 (data not shown) was the same as that originally reported in the sequence of the entire genome of HCMV strain AD169 (Chee et al., 1994) with the exception of nucleotide 146753. In agreement with Smith and Pari (1995), we found that this residue is a cytosine rather than a guanosine that changes the putative in-frame stop codon TAG at position 146751 to the tryptophan codon TAC. We therefore concur with the interpretation of Smith and Pari (1995), that the first in-frame stop codon is at nucleotide 149105 and that gene UL102 has the capacity to encode a protein of 873 amino acids with a molecular mass of approximately 100K.

Purification of proteins. HCMV UL102 and UL54 proteins were extracted in the same buffers, and purified by the same procedures previously used for the homologous HSV-1 UL8 and UL30 proteins (see above). Purification was monitored using the UL102- and UL54-specific antisera 373 and 144 respectively. FIG. 12 shows a Commassie blue stained gel of purified UL102 (lane 2) and UL54 (lane 3). The marker proteins show that the proteins migrate to positions compatible with their predicted sizes.

Additional evidence for the authenticity of the UL102 protein was provided by the specific reaction of immune serum 373, but not the pre-immune serum, with the protein. FIG. 13 shows a western blot of two different extracts from AcUL102-infected Sf cells (EXT-1 and EXT-2) together with peak UL102-containing fractions from the DEAE-sepharose column (DEAE-2) and the hydroxylapatite column (HA-2). The purification procedure removes a number of faster migrating UL102-related protein bands. It is noteworthy that the pre-immune serum does not react with any bands in these same fractions (Lanes 6–9). Alignment of the blot with the Commassie blue stained gel showed that the band that reacted with antibody 144 comigrated with the purified protein and migrated to the same position with respect to the protein markers (alignment not shown).

Additional evidence for the authenticity of the UL54 protein was provided by the specific reaction of immune serum 144, but not the pre-immune serum, with the protein (FIG. 14). Furthermore, the purified protein was able to catalyse incorporation of [$^3$H]dTTP into an poly(dA)-oligo (dT)$_{12-18}$ template as would be expected of the catalytic subunit of the HCMV DNA polymerase (FIG. 15).

Development of an ELISA to measure the UL54/UL102 interaction. To provide evidence that the UL54-specific antiserum 144, directed against the C-terminal 15 amino acids of the protein, might be suitable for measuring the UL54/UL102 interaction, we tested whether antiserum 113, directed against the C-terminal 15 amino acids of HSV-1 UL30 (POL) could be used to detect the HSV-1 UL30/UL8 interaction. As a control we used the UL30-specific MAb 13185 that had previously been used to monitor the HSV-1 interaction. The assay was performed as described previously. Briefly, plates were coated with UL8 and bound UL30 was detected with MAb 13185 followed by HRP-conjugated anti mouse IgG and chromogenic substrate. The absorbance was recorded at 405 nm. The results are shown in FIG. 16 and are presented in groups of 4 bars. Bar 1 shows absorbance in wells with both UL8 and UL30, bars 2, 3 and 4 show the absorbance when UL30, UL8 or both UL8 and UL30 respectively were omitted. Data in groups A and B show the results with and without MAb 13815, and confirm our previous findings showing that the signal is dependent on the presence of HSV-1 UL8, UL30 and MAb 13185. Data in groups C, D, E and F show similar experiments in which the detecting antibody was rabbit serum 113 diluted 10$^3$-, 10$^4$- or 10$^5$-fold or-omitted (No RAb). Bound antibody was detected with HRP-conjugated protein A. The data show that in this assay, the signal is dependent on the presence of HSV-1 UL8, UL30 and the C-terminal antiserum 113. Thus, this C-terminal antiserum can be used to monitor the HSV-1 UL30/UL8 interaction.

These findings suggested that the rabbit serum 144, specific for the C-terminus of HCMV UL54 might enable the HCMV UL54/UL102 interaction to be monitored. The data presented in FIG. 14 indicated that this serum could be diluted 5-fold and give an acceptable signal with UL54 bound directly to wells, and the antibody was accordingly used at that concentration. For the interaction assay, wells were coated with amounts of UL102 ranging from zero to 0.4 µg per well. UL54 was added in amounts ranging from ranging from zero to 0.6 µg per well. The results (FIG. 17) show that the signal: 1) is dependent on the presence of both proteins, 2) increases as the amount of UL102 is increased and 3) increases as the amount of UL54 is increased, up to 0.4 µg per well. We interpret these data as evidence for an interaction between UL54 and UL102.

Inhibition of the UL54/UL102 interaction by UL102 peptides. We wished to demonstrate that peptides at or near the C-terminus of other herpesvirus homologues of HSV-1 UL8 would disrupt the interaction between the homologues of UL8 and POL. To do this, the peptides listed in Table 4 were tested for their ability to block the interaction of HCMV UL102 with HCMV UL54. Peptides, diluted in 100 mM Tris-HCl (pH 8.0) plus 0.1% Tween 20, together with 0.4 µg UL54, were added to microtiter wells pre-coated overnight with 0.4 µg UL102. The amount of UL54 bound was determined after 1 h by measuring the absorbance at 405 nm as described. The absorbance in the absence of any peptide, 1.061±0.033, was determined from six wells. The background absorbance in the absence of any UL54, 0.240±0.025, was also determined from six wells and was subtracted from all values. FIG. 18 shows the results, derived from the average of duplicate wells, for peptides 1 and 2 and a control peptide, RT85. The concentration of each peptide required to reduce UL54-binding by 50% (the $IC_{50}$ value) was determined and is listed in Table 4.

TABLE 1

Properties of UL8-specific monoclonal antibodies

| MAb Designation | Immunological reactivity[a] | | | | Inhibition of POL/ULS interaction |
|---|---|---|---|---|---|
| | ELISA | Immuno-precipitation | Immuno-fluorescence | Western Blot (and region)[b] | |
| 801 | ++ | ++ | ++ | − | − |
| 802 | ++ | − | − | − | − |

TABLE 1-continued

Properties of UL8-specific monoclonal antibodies

| MAb Designation | Immunological reactivity[a] | | | | Inhibition of POL/ULS interaction |
|---|---|---|---|---|---|
| | ELISA | Immuno-precipitation | Immuno-fluorescence | Western Blot (and region)[b] | |
| 803 | ++ | − | − | − | − |
| 804 | ++ | ++ | + | + | − |
| 805 | ++ | ++ | ++ | − | − |
| 807 | ++ | − | − | − | + |
| 809 | ++ | − | − | ++ (region 2) | − |
| 811 | ++ | ++ | ++ | ++ (region 1) | − |
| 812 | ++ | − | + | + (region 1) | − |
| 813 | ++ | + | ++ | − | − |
| 814 | ++ | − | + | ++ (region 2) | + |
| 815 | ++ | − | + | − | − |
| 817 | ++ | ++ | ++ | ++ (region 3) | + |
| 818 | ++ | ++ | ++ | ++ (region 3) | + |
| 819 | ++ | ++ | ++ | ++ (region 3) | + |
| 820 | ++ | ++ | − | − | − |

[a]Reactivity in the immunological assays is subjectively described as: ++ strong; + detectable; − not detectable.
[b]The epitopes recognised by these antibodies were mapped to the following locations within UL8: region 1, amino acids 165–253; region 2, amino acids 470–671; region 3, amino acids 717–750.

TABLE 2

Peptides used in this study

| Peptide | Corresponding residues in UL8 | Sequence | $M_r$[a] | $IC_{50}$[b] (µM) |
|---|---|---|---|---|
| 1 | 739–750 | YPFDDKMSFLFA | 1480 | >250 |
| 2 | 728–750 | AGVWGEGGKFVYPFDDKMSFLFA | 2567 | >250 |
| 3 | 726–750 | VLAGVWGEGGKFVYPFDDKMSFLFA | 2779 | >250 |
| 4 | 724–750 | TGVLAGVWGEGGKFVYPFDDKMSFLFA | 2937 | >250 |
| 5 | 722–750 | VFTGVLAGVWGEGGKFVYPFDDKMSFLFA | 3184 | 66 ± 22 |
| 6 | 724–735 | TGVLAGVWGEGGKFV | 1475 | >250 |
| 7 | 719–738 | IELVFTGVLAGVWGEGGKFV | 2077 | 2.3 ± 2.2 |
| 8 | 714–728 | EILREIELVFTGVLA | 1701 | >250 |
| 7J[c] | − | IVEFLKVGFGTEGGVWLVAG | 2077 | >20 |
| RT85[d] | − | VKLWYQLEKEPIVGA | 1772 | >250 |

[a]Relative molecular mass
[b]The concentration of peptide required to reduce POL binding by 50%
[c]The same amino acids as peptide 7 but in jumbled order
[d]Residues 423–437 of the reverse transcriptase of HIV-1 (strain LAI)

TABLE 3

Properties and epitope mapping of POL-specific monoclonal antibodies

| | | Immunological reactivity | | | | |
|---|---|---|---|---|---|---|
| MAb designation | ELISA | Immuno-precipitation | Immuno fluorescence | Western Blot (and UL30 fragment recognised)[a] | Pattern of reactivity[b] | Deduced epitope location[c] |
| 13088 | + | − | − | +(3) | D | 317–596 |
| 13112 | + | − | − | − | E | |
| 13129 | + | + | − | + (2) | B | 213–307 |
| 13185 | + | + | + | + (5) | A | 976–1071 |
| 13429 | + | + | + | + (5) | A | 976–1071 |
| 13455 | + | − | + | − | F | |
| 13460 | + | − | − | + (2) | D | 213–307 |
| 13479 | + | + | − | − | C | |
| 13488 | + | + | − | + (2) | B | 213–307 |
| 13509 | + | + | − | − | C | |
| 13528 | + | + | − | + (3) | B | 317–596 |
| 13579 | + | − | − | − | E | |
| 13584 | + | − | − | − | E | |
| 13628 | + | + | + | + (6) | A | 1120–1127 |

[a]The numbers in parentheses denote the UL30 fragment recognised. The amino acids present in the fragments are: fragment 1, 1–212; fragment 2, 162–316; fragment 3, 308–658; fragment 4, 597–975; fragment 5, 875–1119; fragment 6, 1072–1145 and fragment 7, 1128–1235 respectively.
[b]Based on the presence or absence of reactivity in immunoprecipitation, immunofluorescence and western blotting assays (see discussion).
[c]Based on western blot reactivity with fragments of the UL30 expressed in E. coli.

TABLE 4

Peptides used in Example 3

| Peptide | Corresponding residues in UL102 | Sequence | $M_r$[a] | $IC_{50}$[b] ($\mu$M) |
|---|---|---|---|---|
| 1 | 844–873[d] | DEWRSLAVDAQHAAKRVASECLRFFRLNA | 3413 | 40 |
| 2 | 838–863 | TWLEERDEWRSLAVDAQHAARRVAS | 3052 | 45 |
| RT85[c] | | VKLWYQLEKEPIVGA | 1772 | >200 |

[a]Relative molecular mass
[b]The concentration of peptide required to reduce HCMV UL54-binding by 50%
[c]Residues 423–437 of the reverse transcriptase of HIV-1 (strain LA1)
[d]Contains R to K substitution at residue 859

REFERENCES

ATHERTON, E. and SHEPPARD, R. C. (1989). *Solid phase peptide synthesis: a practical approach.* IRL Press, Oxford.

BOEHMER, P. E. and LEHMAN, I. R. (1993). Physical interaction between the herpes simplex virus 1 origin-binding protein and single-stranded DNA-binding protein ICP 8. *Proceedings of the National Academy of Sciences, USA* 90, 8444–8448.

BOEHMER, P. E., CRAIGIE, M. C., STOW, N. D. and LEHMAN, I. R. (1994). Association of origin-binding protein and single-stranded DNA-binding protein, ICP 8, during herpes simplex virus 1 DNA replication in vivo. *Journal of Biological Chemistry* 269, 29329–29334.

BROWN, M. and FAULKNER, P. (1977). A plaque assay for nuclear polyhedrosis viruses using a solid overlay. *Journal of General virology* 36, 361–364.

CALDER, J. M. & STOW, N. D. (1990). Herpes simplex virus helicase-primase: the UL8 protein is not required for DNA-dependent ATPase and DNA helicase activities. *Nucleic Acids Research* 18, 3573–3578.

CALDER, J. M., STOW, E. C. & STOW, N. D. (1992). On the cellular localization of the components of the herpes simplex virus type 1 helicase-primase complex and the viral origin-binding protein. *Journal of General Virology* 73, 531–538.

CHALLBERG, M. D. (1991). Herpes simplex virus DNA replication. *Seminars in Virology* 2, 247–256.

COEN, D. M. (1992). Molecular aspects of anti-herpesvirus drugs. *Seminars in Virology: antiviral therapies*, Saunders Scientific Publications 3, 3–12.

COHEN, E. A., GAUDREAU, P., BRAZEAU, P. and LANGELIER, Y. (1986).

Specific inhibition of herpesvirus ribonucleotide reductase by a nonapeptide derived from the carboxy terminus of subunit 2. *Nature, London* 321, 441–443.

CRUTE, J. J., BRUCKNER, R. C., DODSON, M. S. and LEHMAN, I. R. (1991). Herpes simplex 1 helicase-primase. Identification of two nucleocapsid triphosphatase sites that promote DNA helicase action. *Journal of Biological Chemistry* 266, 21252–21256.

CRUTE, J. J., TSURUMI, T., ZHU, L., WELLER, S. K., OLIVO, P. D., CHALLBERG, M. D., MOCARSKI, E. S. and LEHMAN, I. R. (1989). Herpes simplex virus 1 helicase-primase: a complex of three herpes-encoded gene products. *Proceedings of the National Academy of Sciences, USA* 86, 2186–2189.

DIGARD, P and COEN, D. M. (1990). A novel functional domain of an alpha-like DNA polymerase. The binding site on the herpes simplex virus polymerase for the UL42 protein. *Journal of Biological Chemistry* 265, 17393–17396.

DIGARD, P., BEBRIN, W. R., WEISSHART, K. and COEN, D. M. (1993). The extreme C terminus of herpes simplex virus DNA polymerase is crucial for functional interaction with processivity factor UL42 and for viral replication. *Journal of Virology* 67, 398–406.

DIGARD, P., WILLIAMS, K. P., HENSLEY, P., BROOKS, I. S., DAHL, C. E. and COEN, D. M. (1995). Specific inhibition of herpes simplex virus DNA polymerase by helical peptides corresponding to the subunit interface. *Proceedings of the National Academy of Sciences, USA* 92, 1456–1460.

DODSON, M. S. & LEHMAN, I. R. (1991). Association of DNA helicase and primase activities with a subassembly of the herpes simplex virus 1 helicase-primase composed of the UL5 and UL52 gene products. *Proceedings of the National Academy of Sciences, USA* 88, 1105–1109.

DODSON, M. S., CRUTE, J. J., BRUCKNER, R. C. and LEHMAN, I.R. (1989). Overexpression and assembly of the herpes simplex virus type 1 helicase-primase in insect cells. *Journal of Biological Chemistry* 264, 20835–20838.

DRACHEVA, S., KOONIN, E. V., and CRUTE, J. J. (1995). Identification of the primase active site of the herpes simplex virus type 1 helicase-primase. *Journal of Biological Chemistry* 270, 14148–14153.

DUTIA, B. M., FRAME, M. C., SUBAK-SHARPE, J. H., CLARK, W. N. and MARSDEN, H. S. (1966). Specific inhibition of herpesvirus ribonucleotide reductase by synthetic peptides. *Nature, London* 321, 439–441.

GORBALENYA, A. E., KOONIN, E. V., DONCHENKO, A. P. and BLINOV, V. M. (1989). Two related families of putative helicases involved in replication, recombination, repair and expression of DNA and RNA genomes. *Nucleic Acids Research* 17, 4713–4730.

GOTTLIEB, J., MARCY, A. I., COEN, D. M. and CHALLBERG, M. D. (1990). The herpes simplex virus type 1 UL42 gene product: a subunit of DNA polymerase that functions to increase processivity. *Journal of Virology* 64, 5976–5987.

HAFFEY, M. L and FIELD, A. K. (1995). Selective inhibition of Cytomegalovirus replication. In: Antiviral Chemotherapy, pp83–126. (Edited by D. J. Jeffries and E. De Clerq). John Wiley and Sons KITTS, P. A., AYRES, M. D. and POSSEE, R. D. (1990). Linerization of baculovirus DNA enhances recovery of recombinant virus expression vectors. *Nucleic Acids Research* 18, 5667–5672.

KLINEDINST, D. K. and CHALLBERG, M. D. (1994). Helicase-primase complex of herpes simplex virus type 1: a mutation in the UL52 subunit abolishes primase activity. *Journal of Virology* 68, 3693–3701.

KOHLER, G. and MILSTEIN, C. (1975). Continuous culture of fused cells secreting antibody of predefined specificity. *Nature, London* 256, 495–497.

LAEMMLI, U. K. (1970). Cleavage of structural proteins during the assembly of the head of bacteriophage T4. *Nature, London* b 680–685.

LIPTAK, L. M., UPRICHARD, S. L. and KNIPE, D. M. (1996). Functional order of assembly of herpes simplex virus DNA replication proteins into prereplicative site structures. *Journal of Virology* 70, 1759–1767.

LUIZZI, M., DEZIEL, R., MOSS, N., BEAULIEU, P., BONNEAU, A-M., BOUSQUET, C., CHAFOULEAS, J. G., GARNEAU, M., JARAMILLO, J., KROGSRUD, R. L., LAGACE, L., McCOLLUM, R. S., NAWOOT, S. and GUINDON, Y. (1994). A potent peptidomimetic inhibitor of HSV ribonucleotide reductase with antiviral activity in vivo. *Nature, London* 372, 695–698.

LUKONIS, C. J. AND WELLER, S. K. (1996). Characterisation of nuclear structures in cells infected with herpes simplex virus type 1 in the absence of viral DNA replication. *Journal of Virology* 70, 1751–1758.

MARSDEN, H. S., CROSS, A. M., FRANCIS, G. J., PATEL, A. H., MacEACHRAN, K. A., MURPHY, M., McVEY, G. L., HAYDON, D., ABBOTTS, A.and STOW, N. D. (1996). The herpes simplex virus type 1 UL8 protein influences the intracellular localisation of the UL52 but not the ICP8 or POL replication proteins in virus-infected cells. *Journal of General Virology*—in press.

MARSDEN, H. S., MURPHY, M., McVEY, G. L., MacEACHRAN, K. A., OWSIANKA, A. M. and STOW, N. D. (1994). Role of the carboxy terminus of herpes simplex virus type 1 DNA polymerase in its interaction with UL42. *Journal of General Virology* 75, 3127–3135.

MATSUURA, Y., POSSEE, R. D., OVERTON, H. A. and BISHOP, D. H. L. (1987). Baculovirus expression vectors: the requirements for high level expression of proteins, including glycoproteins. *Journal of General Virology* 68, 1233–1250.

MCGEOCH, D. J., DALRYMPLE, M. A., DAVISON, A. J., DOLAN, A., FRAME, M. C., MCNAB, D., PERRY, L. J., SCOTT, J. E. & TAYLOR, P. (1988). The complete DNA sequence of the long unique region in the genome of herpes simplex virus type 1. *Journal of General Virology* 69, 1531–1574.

McLEAN, G. W., ABBOTTS, A. P., PARRY, M. E., MARSDEN, H. S. and STOW, N. D. (1994). The herpes simplex virus type 1 origin-binding protein interacts specifically with the viral UL8 protein. *Journal of General Virology* 75, 2699–2706.

McLEAN, G. W., OWSIANKA, A. M., SUBAK-SHARPE, J. K. and MARSDEN, H. S. (1991). Generation of anti-peptide and anti-protein sera: effect of peptide presentation on immunogenicity. *Journal of Immunological Methods* 137, 149–157.

MOSS, N., BEAULIEU, P., DUCEPPE, J-S., FERLAND, J.-M., GAUTHIER, J., GHIRO, E., GOULET, S., GRENIER, L., LINAS-BRUNET, M., PLANTE, R., WERNIC, D., and DEZIEL, R. (1995). Peptidomimetic inhibitors of herpes simplex virus ribonucleotide reductase: a new class of antiviral agents. *Journal of Medicinal Chemistry* b 3617–3623.

OWSIANKA, A. M., HART, G., MURPHY, M., GOTTLIEB, J., BOEHME, R., CHALLBERG, M. and MARSDEN, H. S. (1993). Inhibition of herpes simplex virus type 1 DNA polymerase activity by peptides from the UL42 accessory protein is largely nonspecific. *Journal of Virology* 67, 258–264.

PARRY, M. E., STOW, N. D and MARSDEN, H. S. (1993). Purification and properties of the herpes simplex virus type 1 UL8 protein. *Journal of General Virology* 74, 607–612.

POSSEE, R. D. and HOWARD, S. C. (1987). Analysis of the polyhedrin gene promoter of the Autographa californica nuclear polyhedrosis virus. *Nucleic Acids Research* 15, 10233–10248.

PILLEY, D., Emery, V. C and GRIFFITH, P. D. (1995). Clinical aspects of treatment of cytomegalovirus. In: Antiviral Chemotherapy, pp265–283. (Edited by D. J Jeffries and E. De Clerq). John Wiley and Sons.

QUINLAN, M. P., CHEN, L. B. and KNIPE, D. M. (1984). The intranuclear localisation of a herpes simplex virus DNA binding protein is determined by the status of viral DNA replication. *Cell* 36, 857–868.

ROSE, J. K., BUONOCORE, L. and WHITT, M. A. (1991). A new cationic liposome reagent mediating nearly quantitative transfection of animal cells. *BioTechniques* 10, 520–525.

SCHEAFFER, A. K., HURLBURT, W. W., STEVENS, J. T., BIFANO, M., HAMATAKE, R. K., COLONNO, R. J. and TENNEY, D. J. (1995). Characterization of monoclonal antibodies recognizing anino and carboxy-terminal epitopes of the herpes simplex virus UL42 protein. *Virus Research* 38, 305–314.

SHERMAN, G., GOTTLIEB, J. AND CHALLBERG, M. D. (1992). The UL8 subunit of the herpes simplex virus helicase-primase complex is required for efficient primer utilization. *Journal of Virology* 66, 4884–4892.

STOW, N. D. (1992). Herpes simplex virus type 1 origin-dependent DNA replication in insect cells using recombinant baculoviruses. *Journal of General Virology* 73, 313–321.

STOW, N. D. (1993). Sequences at the C-terminus of the herpes simplex virus type 1 UL30 protein are dispensible for DNA polymerase activity but not for viral origin-dependent DNA replication. *Nucleic Acids Research* 21, 87–92.

STOW, N. D., HAMMARSTEN, O., ARBUCKLE, M. I. and ELIAS, P. (1993). Inhibition of herpes simplex virus type 1 DNA replication by mutant forms of the origin-binding protein. *Virology* 196, 413–418.

TENNEY, D. J., HURLBURT, W. W., MICHELETTI, P. A., BIFANO, M. And HAMATAKE, R. K. (1994). The UL8 component of the herpes simplex virus helicase-primase complex stimulates primer intranuclear localisation of a herpes simplex virus DNA binding protein is determined by the status of viral DNA replication. *Cell* 36, 857–868.

ROSE, J. K., BUONOCORE, L. and WHITT, M. A. (1991). A new cationic liposome reagent mediating nearly quantitative transfection of animal cells. *BioTechniques* 10, 520–525.

SCHEAFFER, A. K., HURLBURT, W. W., STEVENS, J. T., BIFANO, M., HAMATAKE, R. K., COLONNO, R. J. and TENNEY, D. J. (1995). Characterization of monoclonal antibodies recognizing anino and carboxy-terminal epitopes of the herpes simplex virus UL42 protein. *Virus Research* 38, 305–314.

SHERMAN, G., GOTTLIEB, J. AND CHALLBERG,. M. D. (1992). The UL8 subunit of the herpes simplex virus helicase-primase complex is required for efficient primer utilization. *Journal of Virology* 66, 4884–4892.

STOW, N. D. (1992). Herpes simplex virus type 1 origin-dependent DNA replication in insect cells using recombinant baculoviruses. *Journal of General Virology* 73, 313–321.

STOW, N. D. (1993). Sequences at the C-terminus of the herpes simplex virus type 1 UL30 protein are dispensible for DNA polymerase activity but not for viral origin-dependent DNA replication. *Nucleic Acids Research* 21, 87–92.

STOW, N. D., HAMMARSTEN, O., ARBUCKLE, M. I. and ELIAS, P. (1993). Inhibition of herpes simplex virus type 1 DNA replication by mutant forms of the origin-binding protein. *Virology* 196, 413–418.

TENNEY, D. J., HURLBURT, W. W., MICHELETTI, P. A., BIFANO, M. And HAMATAKE, R. K. (1994). The UL8 component of the herpes simplex virus helicase-primase complex stimulates primer synthesis by a subassembly of the UL5 and UL52 components. *Journal of Biological Chemistry* 269, 5030–5035.

TENNEY, D. J., MICHELETTI, P. A., STEVENS, J. T., HAMATAKE, R. K. MATTHEWS, J. T., SNACHEZ, A. R., HURLBURT, W. W., BIFANO, M., and CORDINGLEY, M. G. (1993). Mutations in the C terminus of herpes simplex virus type 1 DNA polymerase can affect binding and stimulation by its accessory protein UL42 without affecting basal polymerase activity. *Journal of Virology* 67, 543–547.

TOWBIN, H., STAEHELIN, T. and GARDA, J. (1979). Electrophoretic transfer of proteins from polyacrylamide gels to nitrocellulose sheets: procedure and some applications. *Proceedings of the National Academy of Sciences U.S.A.* 76, 4350–4354.

WELLER, S. K. (1991). Genetic analysis of HSV genes required for genome replication. In *Herpesvirus Transcription and Its Regulation.* pp 105–135. Edited by E. K. Wagner, Boca Raton: CRC Press.

WU, C. A., NELSON, N. J., McGEOCH, D. J. and CHALLBERG, M. D. (1988) Identification of herpes simplex virus type 1 genes required for origin-dependent DNA synthesis. *Journal of Virology* 62, 435–443.

ZHU, L. and WELLER, S. K. (1992). The six conserved helicase motifs of the UL5 gene product, a component of the herpes simplex virus type 1 helicase primase, are essential for its function. *Journal of Virology* 66, 469–479.

CHEE, M. S., BANKIER, A. T., BECK, S., BOHNI, R., BROWN, C. M., CERNY, R. and HORSNELL, T. (1994). Analysis of the coding content of the sequence of human cytomegalovirus strain AD169. Current Topics in Microbiology and Immunology 154, 125–169.

ERTL, P. F., THOMAS, M. S. and POWELL, K. L. (1991). High level expression of DNA polymerase from herpesviruses. Journal of General Virology 72, 1729–1734.

SMITH, J. A., and G. S. PARI. 1995. (1995). Human cytomegalovirus UL102 gene. *Journal of Virology* 69, 1734–1740.

BISHOP, D. H. L. (1992). Baculovirus expression vectors. Seminars in Virology 3, 253–264.

What is claimed is:

1. An antiviral agent which prevents or hinders replication of a herpesvirus in vitro by specifically binding to POL or UL8, thus inhibiting the association between UL8 and POL, wherein "UL8" is defined as UL8 of HSV-1 or the homologues thereof in other herpesviruses and "POL" is defined as POL of HSV-1 or homologues thereof in other herpesviruses, wherein said agent is a peptide selected from the group of peptides:
   a) VFTGVLAGVWGEGGKFVYPFDDKMSFLFA (SEQ ID NO: 5);
   b) IELVFTGVLAGVWGEGGKFV (SEQ ID NO: 7);
   c) DEWVRSLAVDAQHASKRVASEGLRFFRLNA (SEQ ID NO: 11) and;
   TWLEERDEWVRSLAVDAQHAARRVAS (SEQ ID NO: 12).

2. An antiviral agent as claimed in claim 1 which is a synthetic peptide.

3. A method of preventing replication of a herpesvirus, said method comprising providing an agent able to bind specifically to UL8 or POL thereby inhibiting the association between UL8 and POL in vitro, wherein "UL8" is defined as UL8 of HSV-1 or the homologues thereof in other herpesviruses and "POL" is defined as POL of HSV-1 or the homologues thereof in other herpesvirus, and wherein said agent is a peptide selected from the group of peptides:
   a) VFTGVLAGVWGEGGKFVYPFDDKMSFLFA (SEQ ID NO: 5);
   b) IELVFTGVLAGVWGEGGKFV (SEQ ID NO: 7);
   c) DEWVRSLAVDAQHASKRVASEGLRFFRLNA (SEQ ID NO: 1) and;
   TWLEERDEWVRSLAVDAQHAARRVAS (SEQ ID NO: 12);
   said method comprising adding said agent to said replicating herpesvirus in sufficient quantity to cause said inhibition and monitoring the effect on viral replication and thus determining the presence or extent of said inhibition.

* * * * *

UNITED STATES PATENT AND TRADEMARK OFFICE
CERTIFICATE OF CORRECTION

PATENT NO. : 6,337,074
DATED : January 8, 2002
INVENTOR(S) : Marsden et al.

It is certified that error appears in the above-identified patent and that said Letters Patent is hereby corrected as shown below:

Column 34,
Lines 37 and 38, subparagraph c) should read
-- c) DEWVRSLAVDAQHASKRVASEGLRFFRLNA (SEQ ID NO: 11) and; --

Signed and Sealed this

Seventh Day of May, 2002

Attest:

Attesting Officer

JAMES E. ROGAN
*Director of the United States Patent and Trademark Office*